(12) United States Patent
Lander

(10) Patent No.: US 7,891,246 B2
(45) Date of Patent: Feb. 22, 2011

(54) TRACKING VIBRATIONS IN A PIPELINE NETWORK

(75) Inventor: Paul Lander, Maynard, MA (US)

(73) Assignee: Itron, Inc., Liberty Lake, WA (US)

(*) Notice: Subject to any disclaimer, the term of this patent is extended or adjusted under 35 U.S.C. 154(b) by 0 days.

(21) Appl. No.: 11/149,432

(22) Filed: Jun. 10, 2005

(65) Prior Publication Data

US 2005/0279169 A1     Dec. 22, 2005

Related U.S. Application Data

(63) Continuation-in-part of application No. 10/291,748, filed on Nov. 12, 2002, now Pat. No. 6,957,157, and a continuation-in-part of application No. 10/959,994, filed on Oct. 8, 2004, now Pat. No. 7,668,670.

(51) Int. Cl.
*G01M 3/24* (2006.01)
*G01M 3/00* (2006.01)

(52) U.S. Cl. .................. 73/592; 73/40.5 A; 73/587; 73/861.03; 702/51

(58) Field of Classification Search .............. 73/592, 73/40.5 A, 587, 861.03, 861.77, 275; 702/51, 702/45; 340/605, 870.02, 870.18, 870.19, 340/870.03
See application file for complete search history.

(56) References Cited

U.S. PATENT DOCUMENTS

| | | | |
|---|---|---|---|
| 3,697,970 A * | 10/1972 | Jaxheimer | 340/870.03 |
| 4,019,373 A | 4/1977 | Freeman et al. | |
| 4,083,229 A | 4/1978 | Anway | |
| 4,172,379 A | 10/1979 | van Tilburg et al. | |
| 4,237,454 A | 12/1980 | Meyer | |
| 4,289,019 A | 9/1981 | Claytor | |
| 4,306,446 A | 12/1981 | Fukuda | |
| 4,327,576 A | 5/1982 | Dickey et al. | |
| 4,543,817 A | 10/1985 | Sugiyama | |
| 4,609,994 A | 9/1986 | Bassim et al. | |
| 4,640,121 A | 2/1987 | Leuker et al. | |
| 4,779,458 A | 10/1988 | Mawardi | |
| 4,844,396 A | 7/1989 | Norton | |
| 4,858,462 A | 8/1989 | Coulter et al. | |

(Continued)

FOREIGN PATENT DOCUMENTS

EP    0955531 A1    11/1999

(Continued)

OTHER PUBLICATIONS

Technical Specification WLM-Sensor; WLM-System pat. reg. "An integral and active Water Loss Management."; 1 page (date unknown).

(Continued)

*Primary Examiner*—J M Saint Surin
(74) *Attorney, Agent, or Firm*—Dority & Manning, P.A.

(57) ABSTRACT

A vibration recorder for detecting leaks in a pipeline network includes a sensor operable to receive vibration signals from a pipeline network, and a communication port connected to an automatic meter reader/transmitter ("AMRT"). A processor connected to the communication port and to the sensor is programmed to process the vibration signals and to send data regarding the processed vibration signals to the AMRT using the communication port. The vibration recorder may also include metering functions, and, in some implementations, may also incorporate the functions of the AMRT.

15 Claims, 20 Drawing Sheets

U.S. PATENT DOCUMENTS

| | | | |
|---|---|---|---|
| 4,958,296 | A | 9/1990 | Saitoh et al. |
| 4,977,529 | A | 12/1990 | Gregg et al. |
| 5,010,553 | A | 4/1991 | Scheller et al. |
| 5,038,614 | A | 8/1991 | Bseisu et al. |
| RE33,722 | E | 10/1991 | Scifres et al. |
| 5,058,419 | A | 10/1991 | Nordstrom et al. |
| 5,117,676 | A | 6/1992 | Chang |
| 5,179,862 | A | 1/1993 | Lynnworth |
| 5,205,173 | A | 4/1993 | Allen |
| 5,272,646 | A | 12/1993 | Farmer |
| 5,361,636 | A | 11/1994 | Farstad et al. |
| 5,416,724 | A | 5/1995 | Savic |
| 5,531,099 | A | 7/1996 | Russo |
| 5,541,575 | A | 7/1996 | Virnich |
| 5,544,074 | A | 8/1996 | Suzuki et al. |
| 5,619,192 | A * | 4/1997 | Ayala ............... 340/870.02 |
| 5,675,506 | A | 10/1997 | Savic |
| 5,854,994 | A | 12/1998 | Canada et al. |
| 5,974,862 | A | 11/1999 | Lander et al. |
| 6,082,193 | A | 7/2000 | Paulson |
| 6,424,270 | B1 * | 7/2002 | Ali ..................... 340/870.02 |
| 6,453,247 | B1 | 9/2002 | Hunaidi |
| 6,530,263 | B1 | 3/2003 | Chana |
| 6,553,336 | B1 * | 4/2003 | Johnson et al. ............ 702/188 |
| 6,567,006 | B1 | 5/2003 | Lander et al. |
| 6,611,769 | B2 * | 8/2003 | Olson ...................... 702/45 |
| 6,657,552 | B2 * | 12/2003 | Belski et al. .......... 340/870.02 |
| 6,694,285 | B1 | 2/2004 | Choe et al. |
| 6,820,016 | B2 | 11/2004 | Brown et al. |
| 6,957,157 | B2 | 10/2005 | Lander |
| 7,007,545 | B1 | 3/2006 | Martinek |
| 7,039,532 | B2 * | 5/2006 | Hunter ....................... 702/61 |
| 7,239,250 | B2 * | 7/2007 | Brian et al. ............ 340/870.02 |
| 7,259,690 | B1 * | 8/2007 | Furmidge et al. ...... 340/870.03 |
| 7,263,450 | B2 * | 8/2007 | Hunter ....................... 702/65 |
| 7,596,458 | B2 | 9/2009 | Lander |
| 2002/0193144 | A1 | 12/2002 | Belski et al. |
| 2003/0167847 | A1 | 9/2003 | Brown et al. |
| 2003/0204338 | A1 | 10/2003 | Martinek |
| 2004/0093174 | A1 | 5/2004 | Lander |
| 2006/0036795 | A1 * | 2/2006 | Leach ...................... 710/305 |
| 2007/0234784 | A1 * | 10/2007 | Kates ........................ 73/40 |

OTHER PUBLICATIONS

WLM-Sensor; WLM-System-Description; 1 page (date unknown).
MWM-Martinek Water Management GmbH; WLM—System; http://www.martinek.org/mwm/html/en/wvmsys.htm; printed May 7, 2007, publication date unknown; 1 page.
MWM-Martinek Water Management GmbH; Application; http://www.martinek.org/mwm/html/en/application.htm; printed May 7, 2007, publication date unknown; 1 page.
MWM-Martinek Water Management GmbH; WLM—Sensor; http://www.martinek.org/mwm/html/en/wvmsen.htm; printed May 7, 2007, publication date unknown; 1 page.
MWM-Martinek Water Management GmbH; Modems; http://www.martinek.org/mwm/html/en/modem.htm; printed May 7, 2007, publication date unknown; 1 page.
MWM-Martinek Water Management GmbH; Power—mains supply; http://www.martinek.org/mwm/html/en/power.htm; printed May 7, 2007, publication date unknown; 1 page.
MWM-Martinek Water Management GmbH: Battery; http;//www.martinek.org/mwm/html/en/battery.htm; printed May 7, 2007, publication date unknown; 1 page.
MWM-Martinek Water Management GmbH; Solar Panel; http://www.martinek.org/mwm/html/en/solar.htm; printed May 7, 2007, publication date unknown; 1 page.
MWM-Martinek Water Management GmbH; AQUALYS; http://www.martinek.org/mwm/html/en/AQUALYS.htm; printed May 7, 2007, publication date unknown; 1 page.
International Search Report for PCT International Application No. PCT/US2005/035929 dated Apr. 4, 2006.
H. Schwarze; "Computer supported measuring system for automatic control of pipe networks and leak detection"; Technisches Messen 55(7-8); pp. 279-285; 1988 (Partial Translation included in text).
Supplementary European Search Report dated Mar. 2, 2001, 3 pages.
PCT International Search Report (Application No. PCT/US05/35929), Apr. 4, 2006, 4 pages.
PCT Written Opinion (Application No. PCT/US05/35929), Apr. 4, 2006, 9 pages.
MicroCorr Digital; Leak Detection—*Digital Leak Noise Correlator*; Palmer Environmental; MD Issue 1 Apr. 2001 UK; 8 pages.
Office Action for EP Application No. 05 804 427.2-1236 dated Mar. 1, 2010.

* cited by examiner

Fig. 14

TRACKING VIBRATIONS IN A PIPELINE NETWORK

CROSS-REFERENCE TO RELATED APPLICATIONS

This application is a continuation-in-part application of and claims priority to U.S. application Ser. No. 10/291,748, filed on Nov. 12, 2002 now U.S. Pat. No. 6,957,157 and currently allowed, and U.S. application Ser. No. 10/959,994, filed on Oct. 8, 2004 now U.S. Pat. No. 7,668,670. These applications are incorporated by reference.

TECHNICAL FIELD

This description relates to tracking vibrations in a pipeline network.

BACKGROUND

Pipeline networks are commonly used to distribute fluids, such as water, natural gas, petroleum, and jet fuel. Undetected leaks in such pipeline networks may be expensive and, potentially, hazardous.

SUMMARY

A provided system may include a set of many low-cost, intelligent vibration recorders that are permanently installed on a pipeline network and are components of, or communicate with, flow meters that also are installed on the pipeline network. Each recorder or recorder/flow meter combination is capable of sensing vibrations, obtaining meter readings, and communicating.

When a leak is present in a pipe, a pressure wave emanates from the turbulent source of the leak and travels away from the leak through the wall of the pipe and the fluid in the pipe. This leak signal is attenuated with distance and has a spectral signature (varying energy at different frequencies) that depends on the effective transfer function of the pipe network and the sensor connection. The effective range of the recorder depends on such factors as the pipe pressure, the leak signal strength and the variable background pipe flow and ambient noise levels present at the sensor.

Aspects of the system include installing the recorders on the pipeline network, recording and processing in the recorders, data transport (including meter reading data) from the recorder to a database using the reader and the controller, data analysis in the computer, and visual presentation of the analysis.

Water and other utility companies manage capital and operational expenditures, often with capital expenditures being more available than operational expenditures. Leak detection will yield significant savings in the form of reduced requirements for treatment and plant capacity, lost product, mandatory water use (revenue) restriction due to limited water resources, and reduced risk of catastrophic events. The challenge for water companies is to manage their human and capital resources to achieve sustainable network and leakage management. Currently, leak detection is performed in the field using personnel, vehicles and computerized leak detection and pinpointing equipment. The complete system, including recorders, readers, and controllers, provides the information needed to focus this effort with no additional operational expenditures.

In one general aspect, a vibration recorder for detecting leaks in a pipeline network includes a sensor operable to receive vibration signals from a pipeline network, a communication port connected to an automatic meter reader/transmitter ("AMRT"), and a processor connected to the communication port and to the sensor to receive the vibration signals. The processor is programmed to process the vibration signals and to send data regarding the processed vibration signals to the AMRT using the communication port.

Implementations may include one or more of the following features. For example, the processor may be programmed to emulate a register encoder of a water meter when sending data to the AMRT, and may be programmed to send data regarding the processed vibration signals to the AMRT as a sequence of meter reading values.

The recorder also may include a connection to a register encoder of a water meter, and may be programmed to receive meter reading values from the connection to the register encoder. The processor also may be programmed to determine a type of the register encoder, and to interpret the meter reading values received from the connection to the register encoder based on the determined type of the register encoder. The processor also may be programmed to determine a usage activity pattern based on the meter reading values.

The vibration recorder also may include a pulse detector configured to detect magnetic pulses produced by a water meter. In such implementations, the processor is connected to receive an output of the pulse detector and programmed to generate meter reading values based on the output of the pulse detector. The processor also may be programmed to determine a usage activity pattern based on the output of the pulse detector.

In another general aspect, a vibration recorder for detecting leaks in a pipeline network includes a sensor operable to receive vibration signals from a pipeline network, a wireless transmitter, and a processor connected to the wireless transmitter and to the sensor to receive the vibration signals. The processor is programmed to process the vibration signals and to use the transmitter to transmit data regarding the processed vibration signals, and to generate meter reading values and to use the transmitter to transmit the meter reading values.

Implementations may include one or more of the features discussed above.

The details of one or more implementations are set forth in the accompanying drawings and the description below. Other features will be apparent from the description and drawings, and from the claims.

DESCRIPTION OF DRAWINGS

FIG. 14 is a database table showing parameters of the recorders.

Like reference symbols in the various drawings indicate like elements.

DETAILED DESCRIPTION

Figure 1:
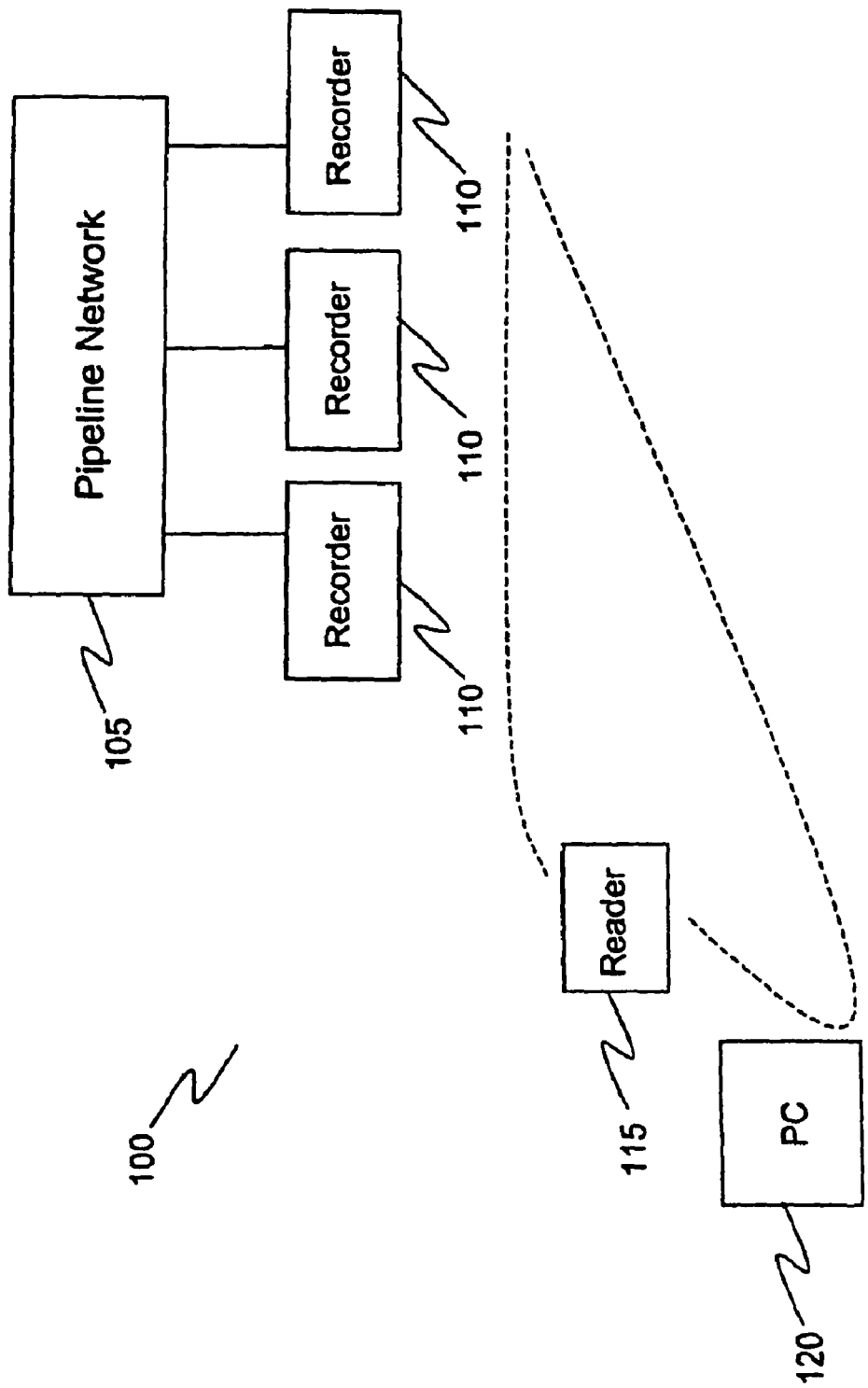
FIG. 1 is a block diagram of a system for tracking vibrations in a pipeline network.

Referring to FIG. 1, a system 100 for tracking vibrations and detecting leaks in a pipeline network 105 includes recorders 110 connected to the pipeline network 105. The recorders 110, which may be components of water meters or automatic meter readers, collect data about vibrations in the pipeline network. One or more readers 115, when brought into proximity with the recorders 110, collect data from the recorders 110. The one or more readers 115 later download data to a computer 120, such as a personal computer (or PC), that processes the data from multiple loggers to detect vibrations and related phenomena (e.g. leaks) in the pipeline network 105.

While the pipeline network 105 is described below in terms of a water system, the pipeline may be another type of network. For example, the system may function with other pressurized fluid-carrying pipeline networks, such as those carrying natural gas, petroleum, and jet fuel.

In general, the recorders 110 are vibration recorders installed permanently on the pipeline network 105. For example, when the pipeline network 105 is a water network, the recorders may be installed permanently on water service lines, typically near the water meters (or as parts of the water meter) in either meter pits or basements. In some implementations, a recorder 110 may be included as part of a water meter or an automatic meter reader. In a gas distribution system, the recorders may be installed permanently on gas service lines, typically near the gas meter, as part of the gas meter, or as part of an automatic meter reader associated with the gas meter. In other networks, such as transmission lines, the recorders may be installed at valves, other convenient access points, or on the pipeline itself. The installation may be underground or above ground, depending on the construction of the pipeline and the facilities needed to communicate with the recorder.

Figure 2:
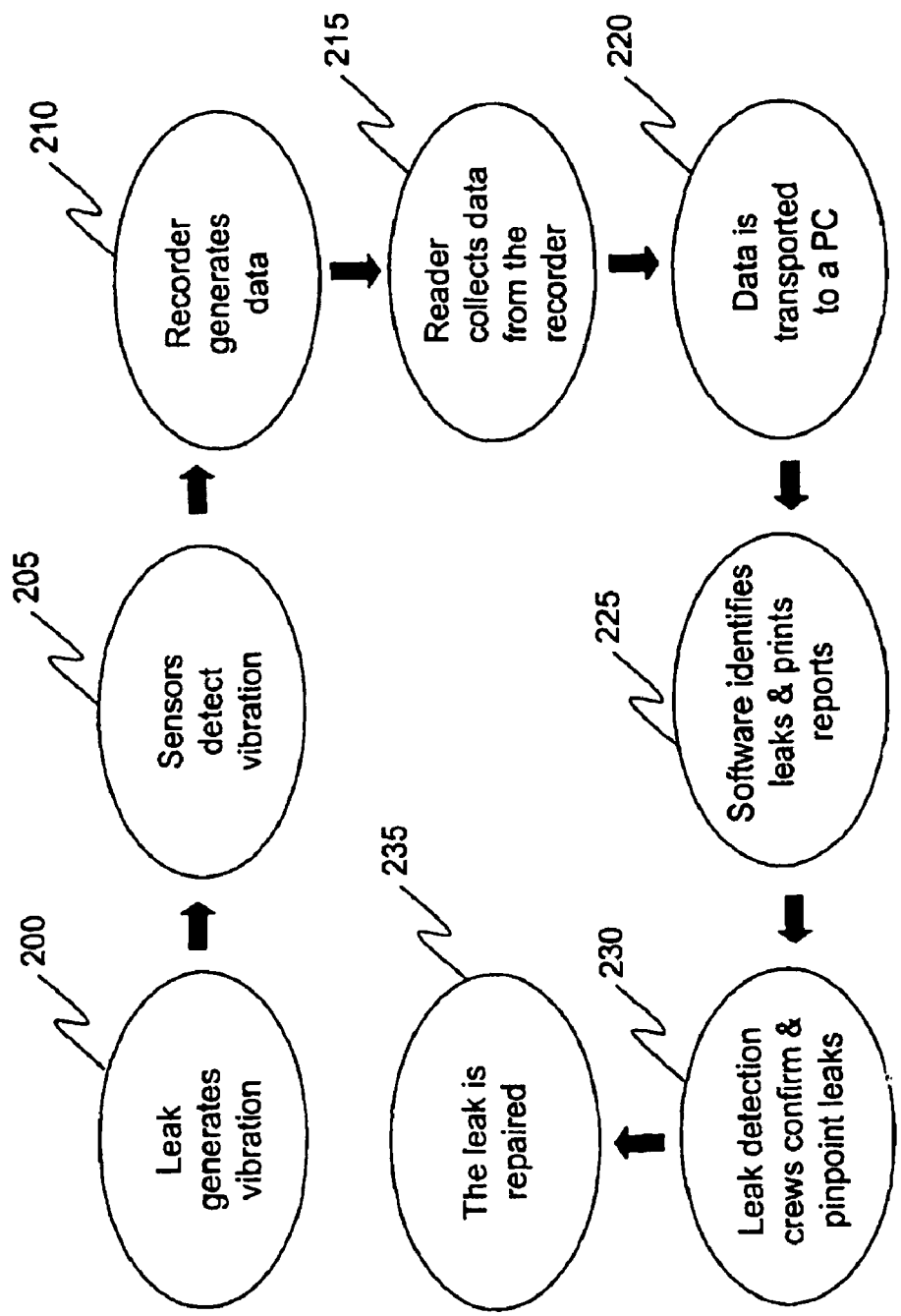
FIG. 2 is a block diagram of the data cycle for the system of FIG. 1.

In summary, and referring to FIG. 2, the data cycle for the system 100 begins with a leak generating vibrations (200). The sensor of the recorder generates a vibration signal corresponding to the vibrations (205) and the recorder generates data corresponding to the vibration signal (210). From time to time, a reader collects the data from the recorder (215). This data is then transported from the reader to a computer through a radio or other link (220). Software on the computer processes the data to identify leaks and generate corresponding reports (225). Repair personnel then use other systems, such as the DigiCorr system available from Flow Metrix, Inc., to confirm and pinpoint locations of the leaks (230). Finally, the pinpointed leaks are repaired (235).

Figure 3:
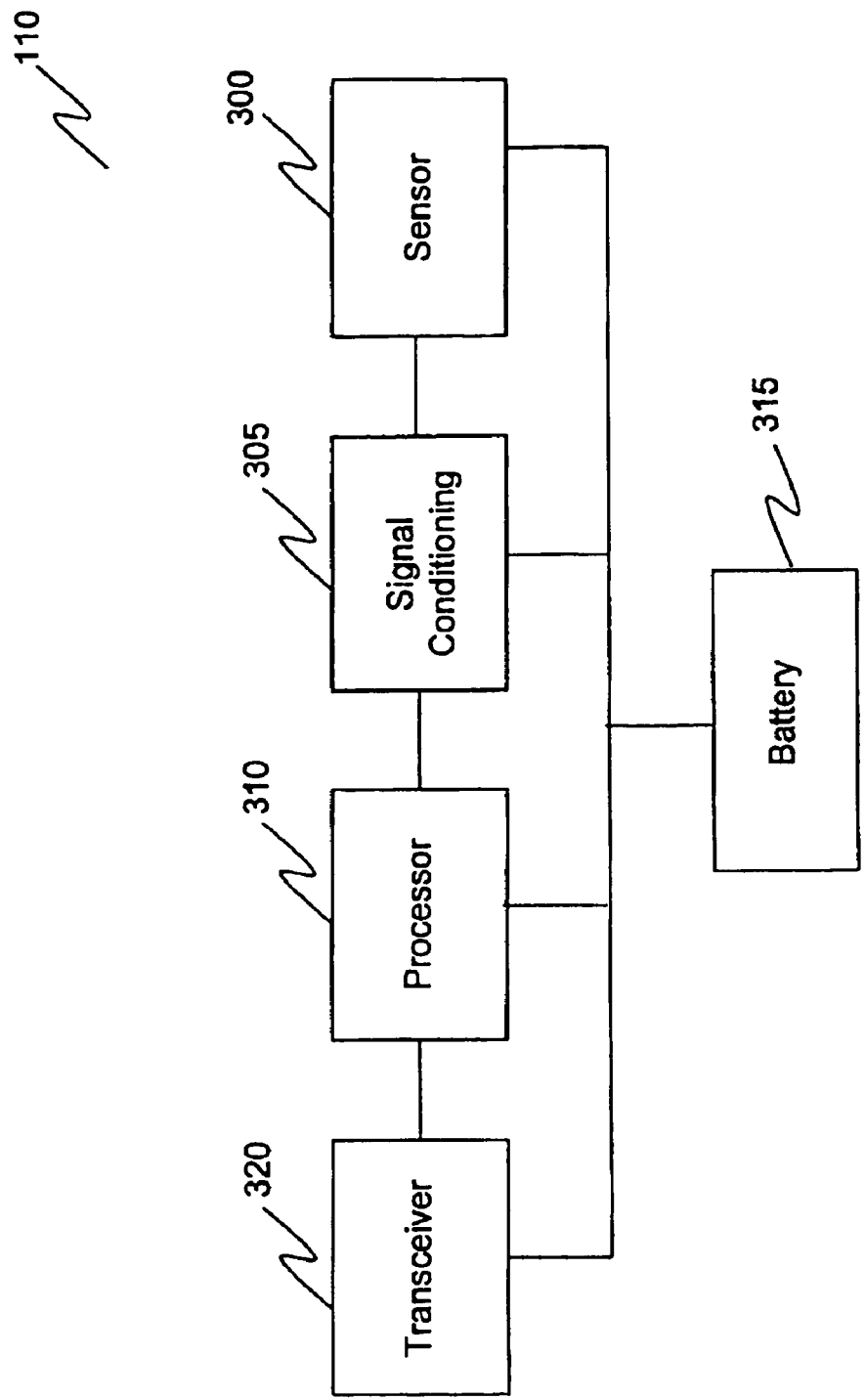
FIG. 3 is a block diagram of a recorder of the system of FIG. 1.

Referring to FIG. 3, in particular implementations, each recorder 110 includes a vibration sensor 300, signal conditioning electronics 305, a processor 310, a battery power supply 315, and a low-power radio transceiver 320. The sensor 300 may be, for example, a piezo-film sensor, a piezo-cable sensor, or some other low-cost vibration sensor. The sensor 300 produces an electrical signal reflective of vibrations in the pipe to which the sensor is attached.

In colder climates, recorders are installed at or as part of the water meter, typically in a basement. In warmer climates, recorders may be installed outdoors in an underground water meter pit. Recorders have an installation density designed to match the expected incidence of leakage. Most leaks occur on service pipes. Typical installations may be, for example, 10 per mile (one every 500 feet), one per 10 services, depending on the terrain, or, in the case of recorders that are included as components of meters or meter readers, one per service. Installations may be more dense in downtown areas and less dense in rural areas. In general, the density of installations may be approximately proportional either to the length of the pipeline network or to the number of services on the network.

Figure 4:
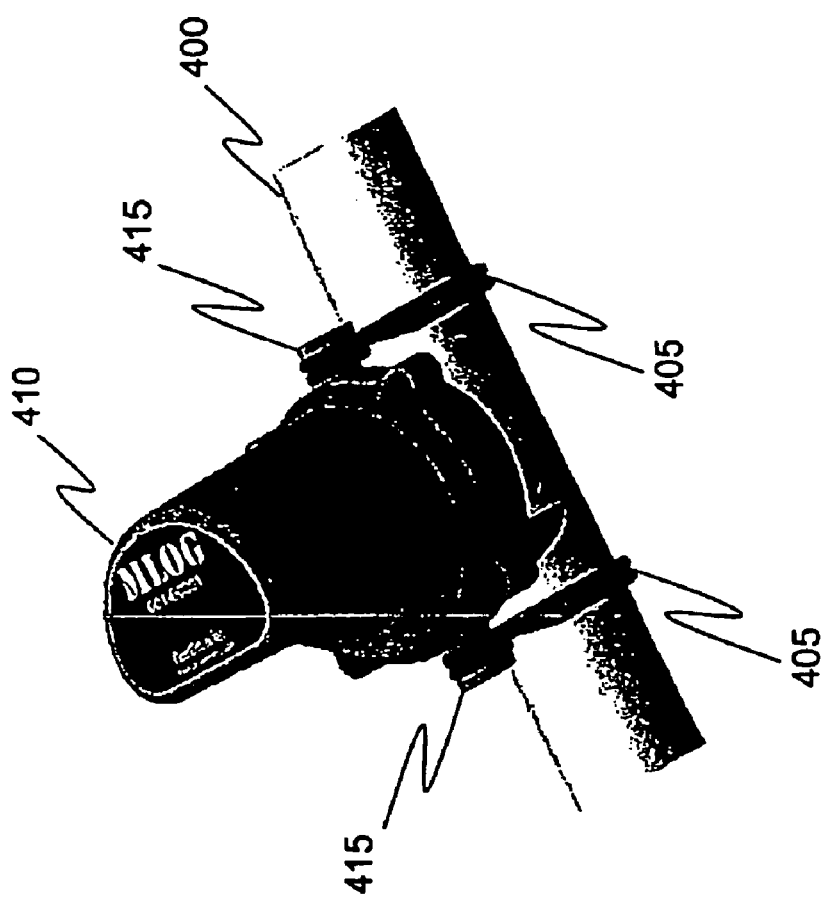
FIGS. 4 and 5 are perspective views showing mounting of the recorder of FIG. 3 on a pipe.
Figure 5:
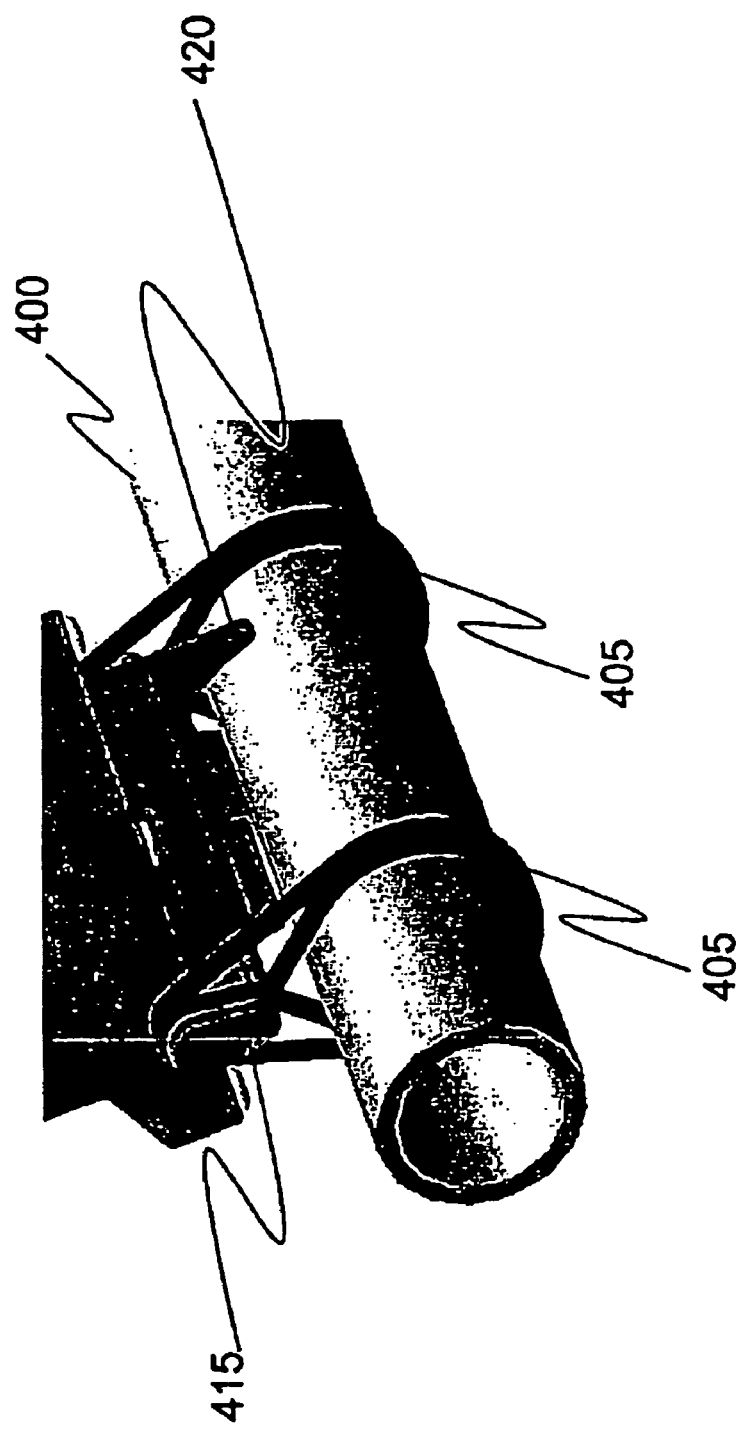

Installation is a significant logistical exercise and can be performed as part of a water meter upgrade program. As shown in FIGS. 4 and 5, one implementation of the recorder 110 is mounted to a pipe 400 by two O-rings 405 that resist weathering and corrosion, require no tools, and are easily and quickly fitted to the pipe. As shown, the housing 410 of the recorder includes connection points 415 that support attachment of the O-rings. In addition, the housing 410 includes curved brackets 420 that ease engagement with the pipe.

A piezo-film vibration sensor, the sensor employed in some implementations, is capable of registering ultra-low vibration levels, but must be directionally-oriented in the line of the flow. The housing design ensures this orientation when installed. Upon installation, the recorder is started with a radio signal from a specially programmed reader.

The signal conditioning electronics 305 receive the signal from the sensor 300, adjust the signal, and pass the adjusted signal to the processor 310. For example, the signal conditioning electronics 305 may be configured to use highpass filtering to reject low frequency vibrations that are present on the pipeline but generally are not produced by leakage. The signal conditioning electronics 305 may be further configured to reject high frequency vibrations through the use of lowpass filtering to improve the signal-to-noise ratio of the vibration recording by restricting high-frequency electronic noise. The signal conditioning electronics 305 also provide analog gain to amplify the signal received from the sensor to a level suitable for digitizing. The degree of analog gain may optionally be set under digital control of the processor 310. The amplified and filtered signal is digitized, using well-known digitizing techniques, either within the signal conditioning electronics 305 or within the processor 310.

The processor 310 generates data representative of the detected vibrations. The processor then stores the data for later transmission using the transceiver 320. The transceiver 320 may be a digital radio transceiver operating at 916 MHz.

The power supply 315 powers the electronic components of the recorder 110. In one implementation, the power supply includes two AA alkaline batteries that provide sufficient power for ten or more years of recorder operation.

The recorder records and processes a series of recordings every night to create a useful representation of the nighttime vibrations. During the night, leak signals are maximized due to minimal usage flow and hence maximal pipe pressure. Background and ambient noise is also minimal. The nighttime representation aims to exclude transient vibrations due to water usage or background noise and to characterize the pipe vibrations present during the quietest part of the night, whenever this occurs. The signal generated at the quietest point of the night may be referred to as the quiescent pipe signal.

Figure 6:
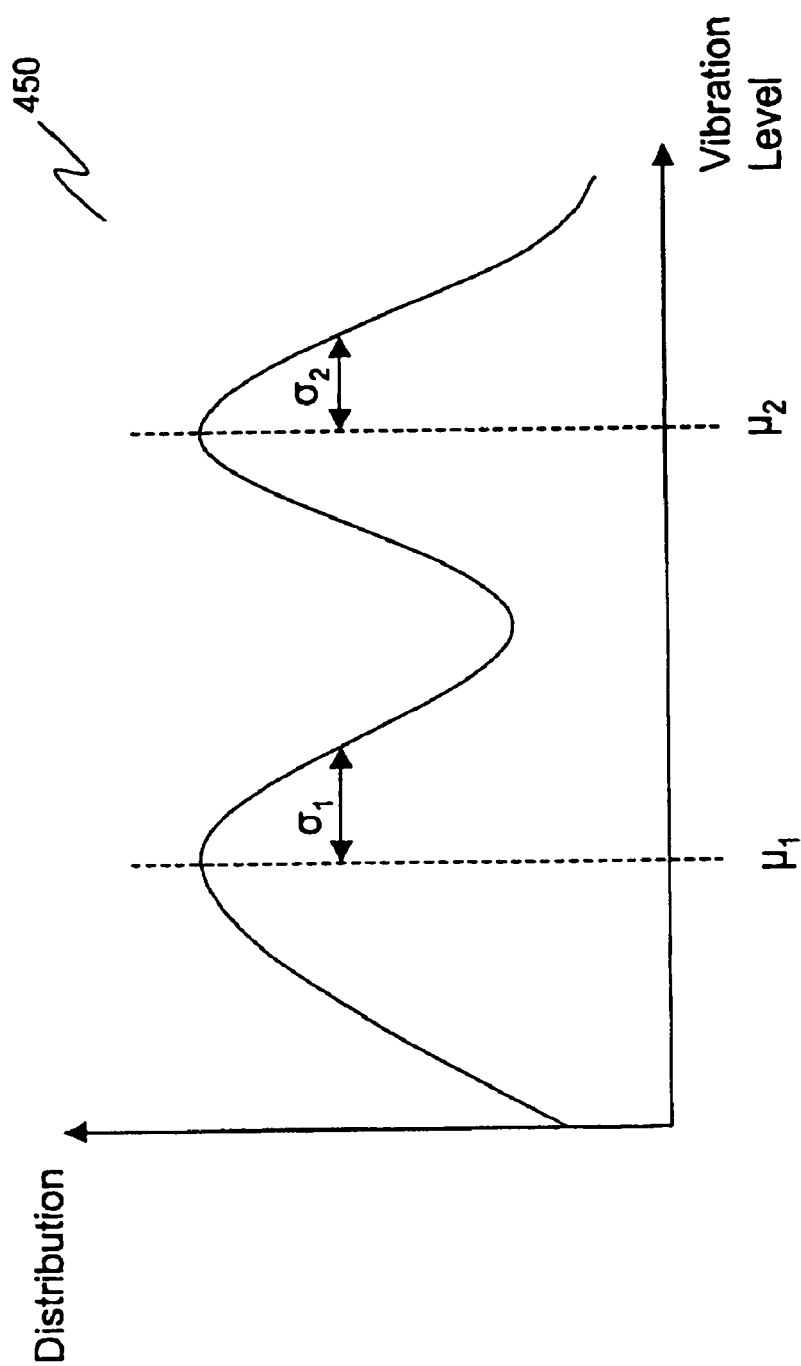
FIG. 6 is a graph showing an example of the nighttime distribution of the recorded vibration level from a single recorder.

Referring to FIG. 6, a graph 450 shows a possible distribution of the recorded vibration level, sampled at many times during a single night by a single recorder. Visualizing the distribution of the recorded vibration level allows interpretation of the nighttime vibration activity. For example, as shown in FIG. 6, background vibration activity may be represented by the apparent normal distribution with mean $\mu_1$ and standard deviation $\sigma_1$. When leakage is present, the mean vibration level $\mu_1$ may be high compared to situations where leakage is not present and the standard deviation of the background vibration activity $\sigma_1$ will tend to be small compared to $\mu_1$ and compared to situations where leakage is not present. Background vibration activity may include transient or sporadic events from causes such as irrigation systems (sprinklers), nighttime usage, pumps, and other vibration sources. The graph 450 shows a possible bi-modal distribution which includes the effects of this transient activity represented by the apparent normal distribution with mean $\mu_2$ and standard deviation $\sigma_2$. Other forms of the distribution of nighttime vibration activity may occur, including, for example, a widened or skewed distribution, or activity that follows a non-normal parametric or a non-parametric distribution.

Figure 7:
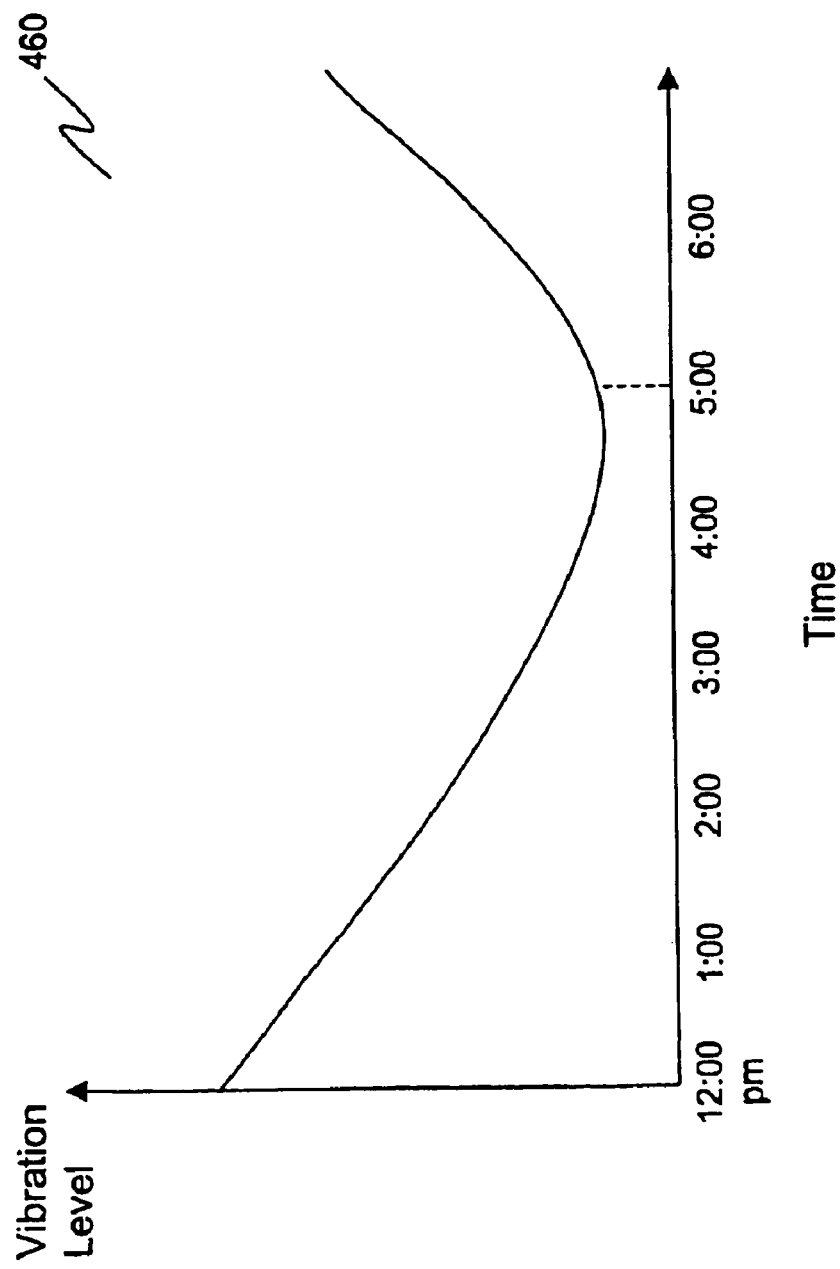
FIG. 7 is a graph showing an example of the nighttime recorded vibration level from a single recorder.

Referring to FIG. 7, the nighttime vibration activity also may be shown as a graph 460 that expresses the relationship between the vibration level and the time of day. A minimum vibration level is presumed to occur at some time during the night and corresponds to the quiescent pipe signal. Visualizing the nighttime activity as a time series allows interpretation of continuous and transient aspects of the nighttime vibration activity.

Other advantages of the visualization capabilities shown in FIGS. 6 and 7 are apparent. For example, unintended usage such as drawing water from fire systems may be detected from examination of the recorded vibrations. The theft or unauthorized usage of product from water, gas, petroleum, or other pipelines may also be detected from examination of the recorded vibrations. Other applications of the system are readily apparent. For example, the recorded vibrations can be used to document and visualize an approximate usage profile of product at a particular point from a pipeline over a particular time period. Comparison of recordings from two or more such time periods can be used to detect changes in the usage profile at a particular point from a pipeline.

The representation of nighttime vibrations may include, but is not limited to, the following parameters: absolute vibration level of the quiescent pipe signal, frequency content of the quiescent pipe signal, distribution of frequency content during the nighttime period, and a comparative measure of these parameters with what has been historically recorded. The goal of the signal processing is to reduce the available nighttime data (30 million bytes for two hours at 4,000 samples per second and one byte per sample) to a characterization or compression of the useful information contained within 64 to 4096 bytes.

Referring again to FIG. 1, in one implementation, each recorder 110 independently makes a series of vibration recordings every night. In general, a recorder may be able to sense vibrations from a distance of up to 500 feet or greater. The recordings are processed to produce a useful representation of the nighttime vibration levels. For example, the recorder 110 may be configured to monitor vibrations at night, process the monitored vibrations, and enter a low-power SLEEP state during the day and at all times when not recording or communicating.

In one implementation, vibration signals are digitized by the processor 210 at a sampling rate of 2,048 Hz. Recording begins at 12:15 am and occurs once per minute until 4:30 am for a total of K=256 recordings. Each recording lasts for one second and is denoted by $x_k(i)$, where k is the recording number and i is the sample number within the recording. Vibrations from pipes typically manifest as pseudo-random stochastic processes, sometimes with a specific spectral structure. Accordingly, each recording may be statistically processed to extract useful information with a reduced storage requirement. One useful method is to compute the mean absolute value of the recording, defined as:

$$E[|x_k(i)|] = \sum_{i=1}^{N} |x_k(i)|/N = \overline{|x_k|}$$

where E[] represents mathematical expected value and the recording is composed of N=2048 samples. If it is assumed that the pipe vibration signal follows a statistically normal distribution, then the values of $\overline{|x_k|}$ resulting from each of the K recordings will follow a statistical chi-square distribution. It is useful to define the following quantities:

$$\mu_q = \sum_{k=1}^{K} \overline{|x_k|}/K$$

and $$\sigma_q = \sqrt{\sum_{k=1}^{K} (\overline{|x_k|} - \mu_q)^2 / K}$$

where $\mu_q$ and $\sigma_q$ are, respectively, the mean and standard deviation of this assumed chi-square distribution considered for the ensemble of K recordings made on day q. In the presence only of flow noise, it has been determined that the relationship between $\mu_q$ and $\sigma_q$ is specific, namely that $\mu_q$ is approximately equal to $\sigma_q$. In the presence of vibrations due to leakage or transient phenomena, the distribution may no longer follow an approximate chi-square form. In this instance, it is useful to store enough information to approximate the form of the distribution of $\overline{|x_k|}$. One example of such an approximation is to compute the values of the bins of a histogram that approximately follows the distribution of $\overline{|x_k|}$. This procedure first defines the boundaries of 2p bins as $\mu_{q-1} \pm na\sigma_{q-1}$, where n ranges from 1 to p and a is a constant, e.g. 0.2. By counting the number of occurrences when $\overline{|x_k|}$ falls within each bin, either a parametric or a non-parametric distribution for $\overline{|x_k|}$ may be approximated. The values of $\mu_{q-1}$ and $\sigma_{q-1}$ are used as a starting point for the distribution computed on day q. This assumes that the mean and standard deviation of the distribution may not differ significantly from day q−1 to the following day, q.

Another useful reduction of the set of vibration recordings is the value of $\overline{|x_k|}$ corresponding to either the quietest or some other desirable characteristic of any recording made during the night. This parameter may correspond to the quiescent pipe signal and may be termed the quiescent parameter. The quiescent parameter will be useful assuming that the recording duration is sufficiently long that $x_k(i)$ can be considered an accurate reflection of the pipe vibration signal present at recording time k. Alternatively, a useful subensemble of the ensemble of K values of $\overline{|x_k|}$ may be used to compute the quiescent parameter. For example, it may be useful to compute the quiescent parameter by averaging a number of values of $\overline{|x_k|}$ corresponding to, for example, the quietest recordings made during the night.

Pipe vibration signals may contain different energies at different frequencies. It is useful to form a representation of the variation of vibration energy versus frequency, denoted by X(m), where m represents a discrete frequency. Many methods exist for estimating X(m). These include application of the Fourier transform, application of other numerical transforms, processing the recorded data with difference equations to emphasize a particular frequency band, and other well-known numerical digital signal processing methods. Segmentation of the pipe vibration signal into one or more discrete frequency bands can allow a discrimination of signal components. For example, $x_k(i)$ can be segmented into $x_k^v(i)$, where v ranges from 1 to V and represents a number of discrete frequency bands. These bands may be determined using a so-called basis set, including for example an octave filter bank or a wavelet transform. All of the processing methods described above and performed with $x_k(i)$ may equally well be performed with $x_k^v(i)$ (i.e. discrete frequency bands of the pipe vibration signal may be processed individually or jointly).

Due to the stochastic nature of pipe vibration signals and the transient nature of other vibrations, the parameters described above may not always be reliable indicators of leakage and other vibration phenomena. An important aspect of the described techniques is the ability of the recorder to adapt to its environment. The recorder performs such an adaptation by taking into account the changes of vibration signals experienced over one or more nights. Any quantitative parameter, y, (including but not limited to the parameters described) may be tracked on a night-by-night basis as follows:

$$\overline{y}_q = \frac{1}{R}y_q + \frac{R-1}{R}\overline{y}_{q-1}$$

where $y_q$ is the parameter to track on day q, R is the number of days over which to track the parameter, and $\overline{y}_q$ is the weighted average of the parameter computed for day q. The variable R may be referred to as the tracking period, measured in days. If the parameter being tracked, y, is, for example, vibration level, and R is equal to 7, then $\overline{y}_q$ will be a weighted average of the vibration level over the last 7 days. The parameter $\overline{y}_q$ is thus useful because it effectively 'remembers' the vibration level for up to 7 days. If the vibration level suddenly changes on day q, then $\overline{y}_q$ can be usefully compared to $y_q$ to detect this sudden change.

The variable R may also be set to, for example, 14, 30, or 90 days, or some other time period. Denoting the tracked parameter with the tracking period, R, as $\overline{y}_q^R$, a matrix of tracked parameters may be defined with several different parameters, each tracked over several different tracking periods. The different tracking periods allow comparison of the current value of any parameter, $y_q$, with its weighted average value, $\overline{y}_q^R$, computed over R days. The comparison will be most sensitive to changes that have evolved over approximately R days. For example, if a leak in a pipeline develops over the course of a month, there may not be a significant change in a parameter y measured from night to night; however, the comparison of $\overline{y}_q^{30}$ with $y_q$ can be expected to be significant. Similarly $\overline{y}_q^{90}$ may be expected to track seasonal changes in parameter y.

This method of tracking a parameter offers several advantages. For example, updating and storing in the memory of the recorder a small matrix of parameters y, each recorded over a number of different tracking periods R, obviates the need to store the values of individual parameters for every day. This is advantageous in that less power is required to transmit a smaller amount of data from the recorder and less memory is required in both the recorder and the reader. The tracking period R in the recorder may be programmed using the reader.

It is not necessary to program the recorder with specific rules for determining whether a particular characteristic of a parameter may be indicative of normal phenomena, including, for example normal flow, environmental noise, pump noise and other normal phenomena, or whether the parameter may be indicative of abnormal phenomena such as, for example, leakage or unauthorized usage. The characteristics of parameters generally vary unpredictably from pipe to pipe, from location to location, and according to the season of the year, pressure, characteristics of the pipe, and other factors. For example, a moderate or loud vibration on a pipe may be due to higher flow, a larger pipe, construction occurring in the vicinity, a fire hydrant or pipeline flushing program, leakage, or some other cause. The method of tracking enables the recorder to adapt to its environment. The recorder is able to provide both the parameters of the recorded vibrations and the tracking information, allowing subsequent analysis to interpret both, either individually or together. The method of tracking is therefore able to take into account unexpected or unpredictable phenomena occurring either permanently or temporarily over any arbitrary time period.

Water distribution systems often experience varying seasonal flows due to irrigation and other seasonal demands. Similarly, gas distribution systems often experience varying seasonal flows due to heating and other seasonal demands. Another useful advantage of the method of tracking is to be able to perform seasonal adjustments to the recorders' data, thereby taking into account either predictable or unpredictable variations occurring over any arbitrary time period.

Referring again to FIG. 1, in particular implementations, a reader 115 is brought into proximity with a recorder 110 from time to time. For example, the reader 115 might be carried by a meter reader, mounted to a utility vehicle, or kept by a homeowner. The reader 115 may be a device that, for example, weighs approximately three ounces and is the size of a pager, or a device attached to or incorporated in a meter reading device.

Figure 8:
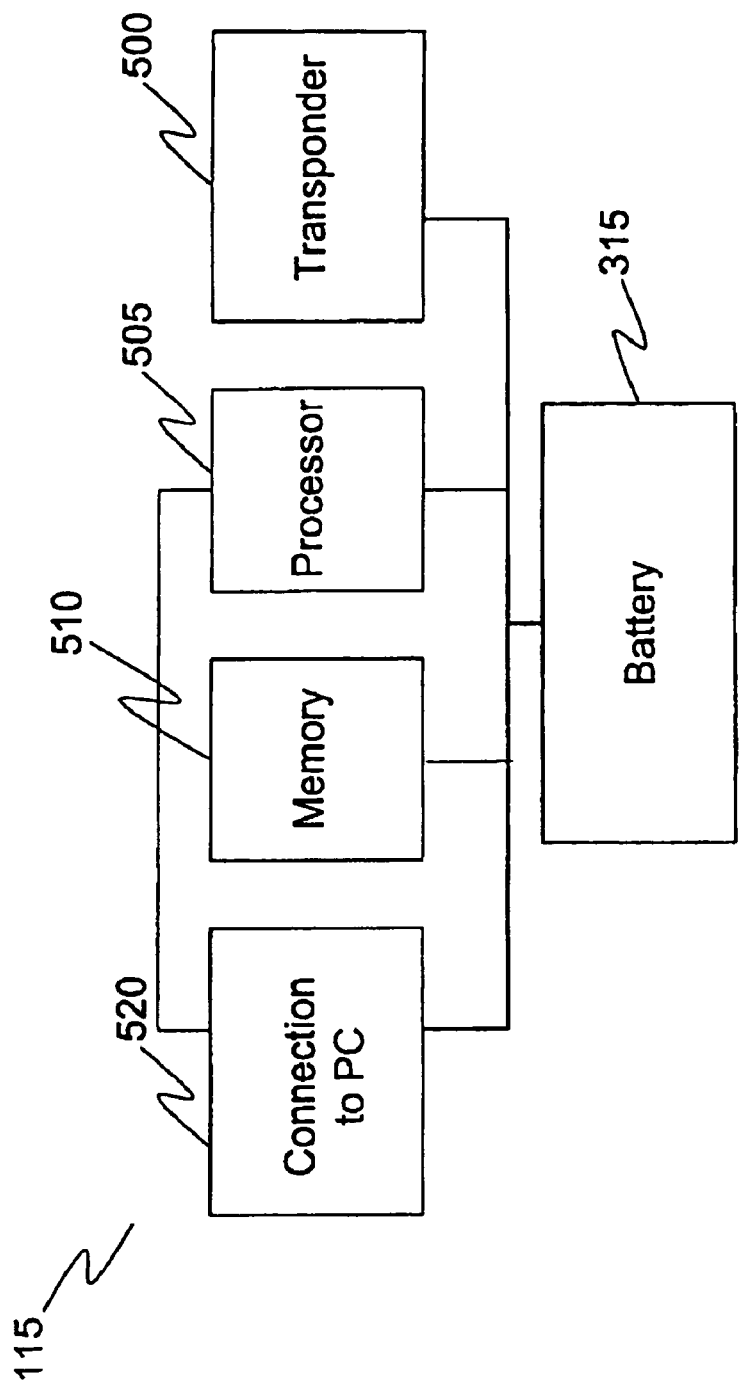
FIG. 8 is a block diagram of a reader of the system of FIG. 1.

Referring to FIG. 8, the reader includes a transponder 500, a processor 505, a memory 510, a battery 515, and a computer connection 520. The transponder 500 periodically transmits (e.g. once every 10 seconds) a radio message that may be referred to as a broadcast 'PING'. For example, in an implementation involving a water system, a meter reader carries a reader 115. This device transmits a frequent PING by radio to wake up any recorders 110 within radio range. In one implementation, the radio range is 75 feet.

If the recorder receives this PING while in the low-power SLEEP state, the recorder wakes up and transmits an acknowledgement that includes the recorder's processed results. The reader 115 receives the acknowledgement and, under control of the processor 505, stores the processed results in memory 510. In one implementation, a reader has storage capacity for results from on the order of 16,000 different recorders. This data transport from the recorder to the reader is completely automatic and requires no special action on the part of the meter reader as he or she performs his or her normal tasks. Both the recorder and the reader manage power optimally so as to conserve the life of the battery 315 (FIG. 3).

The reader 115 also may be operable to upgrade or modify the software of a recorder through transmission of a message to the recorder. This message may be transmitted in response to an acknowledgement received from the recorder.

The reader 115 may be connected to the computer 120 through the computer connection 520, which may be a wired or wireless connection 520. Upon connection, processed recorder results stored in the reader's memory 510 are transmitted to the computer 120 for further processing. In one implementation, the transponder 500 also operates as the computer connection 520.

For example, the meter reader may deposit the reader in the office at the end of the working day. The processed data from all recorders visited by one or more meter readers is now available in one or more readers. The one or more readers may be connected directly to a computer at this point to transfer this data to a computerized database.

Figure 9:
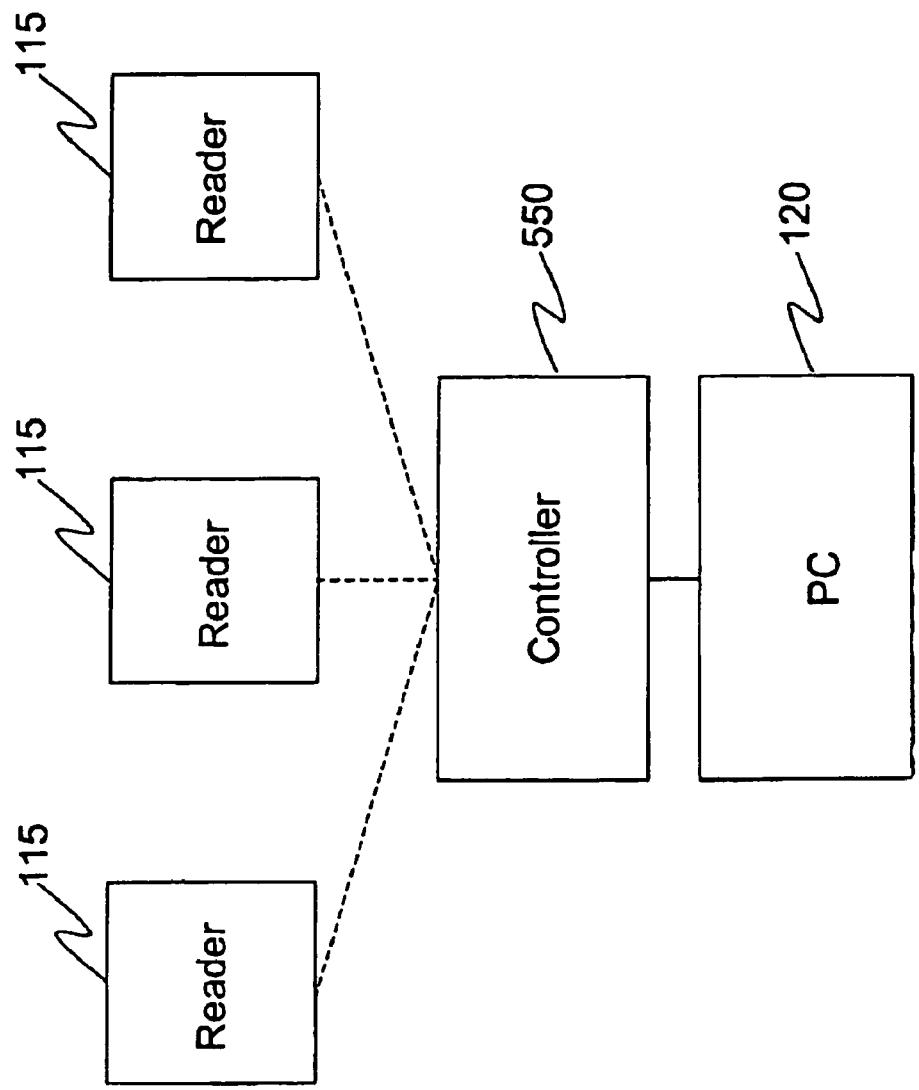
FIG. 9 is a block diagram of a controller of the system of FIG. 1.

Referring to FIG. 9, the computer 120 may optionally include a controller 550 that is operable to communicate with multiple readers 115 to collect processed recorder results and deliver the processed recorder results without human action. For a water company, for example, this accomplishes collecting vibration data from many service point locations and bringing the data to a central computer with no human action other than that normally engaged in for the purposes of reading the water meters.

The controller 550 may be a special form of reader 115 that is electronically connected to a computer 120. During the night, the computer causes the controller to establish radio communication with all readers present. The controller collects the data by radio from the readers and transfers this data to a computerized database.

The computer 120 includes software that may be used to create an information profile for each recorder. This profile may include information useful for maintaining the system, such as the deployment date, the last reading date, and the map/GPS location of the recorder, as well as information for interpreting the processed results, such as the type and size of pipe on which the recorder is installed, the water main connected to that pipe, the type of location (e.g. residential, industrial, urban or rural), and a leakage history for that area.

The software automatically computes a leak index (e.g. a value between 0 and 100) for each recorder, using a combination of processed results and information profiles from one or more recorders. A leak status can be assigned by quantizing the leak index, with each leak status being assigned a different color for display purposes. For example, a leak index of 0-60 may be designated as representing no leak and assigned the color green, a leak index of 60-80 may be designated as representing a possible leak and assigned the color yellow, and a leak index of 80-100 may be designated as representing a probable leak and assigned the color red.

The leak index may be based on individual recorder processed results, such as absolute levels of vibration, consistent patterns of vibration over time, gradually increasing levels of vibration over time, a sudden increase in vibration levels, or changes in spectral composition of the recorded vibrations. These contributors are based on a priori information (i.e. generally available knowledge about the relationship between leaks and pipe vibrations).

The leak index also may be based on the processed results of a set or subset of recorders, such as the loudest recorders; the recorders with the widest frequency content; the recorders with the greatest changes in level or frequency content over a time period of, for example, 7, 30 or 90 days; or the recorders within a subset, such as a type of location or a type of connected pipe, with processed results that are unusual (i.e. outliers in the statistical distribution of the subset). The leak index may be further impacted by network factors, such as leak size, sensitive location (e.g. museum basement), and known profile information, such as leakage history, the presumed likelihood of a leak at the recorder's location, and pipe size, age, and pressure.

Quantizing the leak index (0-100) to a leak status (green, yellow, red) aids leakage management. The quantization may be based on, for example, operations and maintenance resources. For example, in a 1,000-mile network, budgetary constraints may dictate how many leak pinpointing investigations can be conducted in a meter-reading cycle. The system can be set to generate a fixed number of probable leaks based on available resources (i.e., the system can be configured to detect the largest number of most likely leaks that can be investigated with available resources).

The quantization also may be based on leakage minimization so as to provide the most leakage recovered per operating dollar spent. This approach implies using all data to optimize the rate of true positive leak identifications.

The quantization also may consider network optimization/leakage management. In particular, the leak status may be set using the current estimate of leakage density within the network as a whole. For example, consider a network with 1,000 miles of water mains, 100,000 metered accounts, and one recorder installed on average for every 10 meters, i.e. 10 recorders per mile. Assuming that the network has 500 leaks, the network-wide probability of a recorder hearing a leak is approximately five percent. On this basis, with a total of 10,000 recorders, the percentage of recorders assigned a leak status of red would be 500, or five percent of all recorders.

Figure 10:
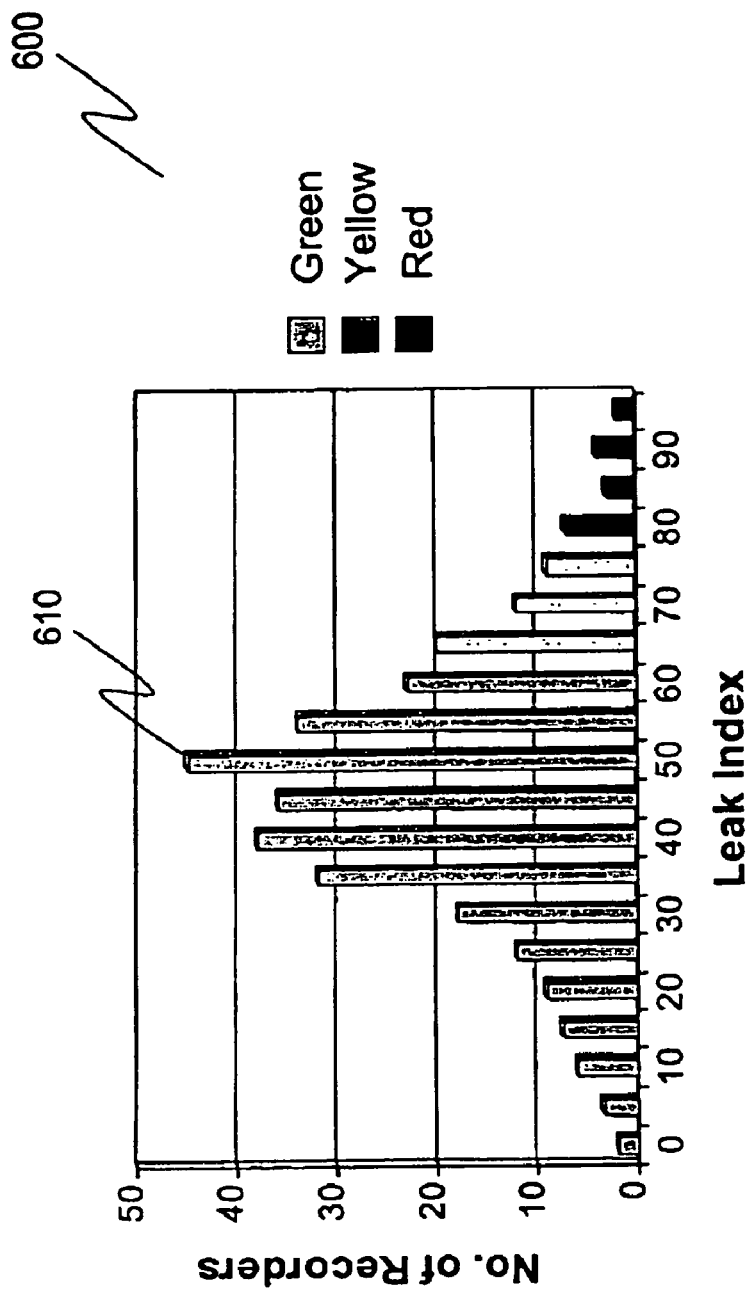
FIG. 10 is a graph showing a distribution of a leak index among all the recorders in a system.

Referring to FIG. 10, a graph 600 illustrates the distribution of a leak index (or any other quantitative parameter, such as vibration level) from all recorders or a subset of recorders. The graph 600 shows, as an example, a statistically normal distribution of the leak index among all the recorders in the system. The graph also shows approximately how many recorders are assigned a green, yellow, or red leak status according to the particular quantization used to create the graph. Specifically, referring again to FIG. 10, the horizontal axis of the graph represents leak index values running from left to right. Each bar 610 represents the number of recorders (the units of the vertical axis) occupying a particular range of leak index values. The color of the bar (green, yellow, or red) represents the leak status of all recorders occupying the particular range of leak index values corresponding to that bar. If the quantization relationship between the leak index (or another quantitative parameter used to create the graph) and the leak status is changed, the approximate number of recorders assigned a particular leak status can be easily visualized.

Figure 11:
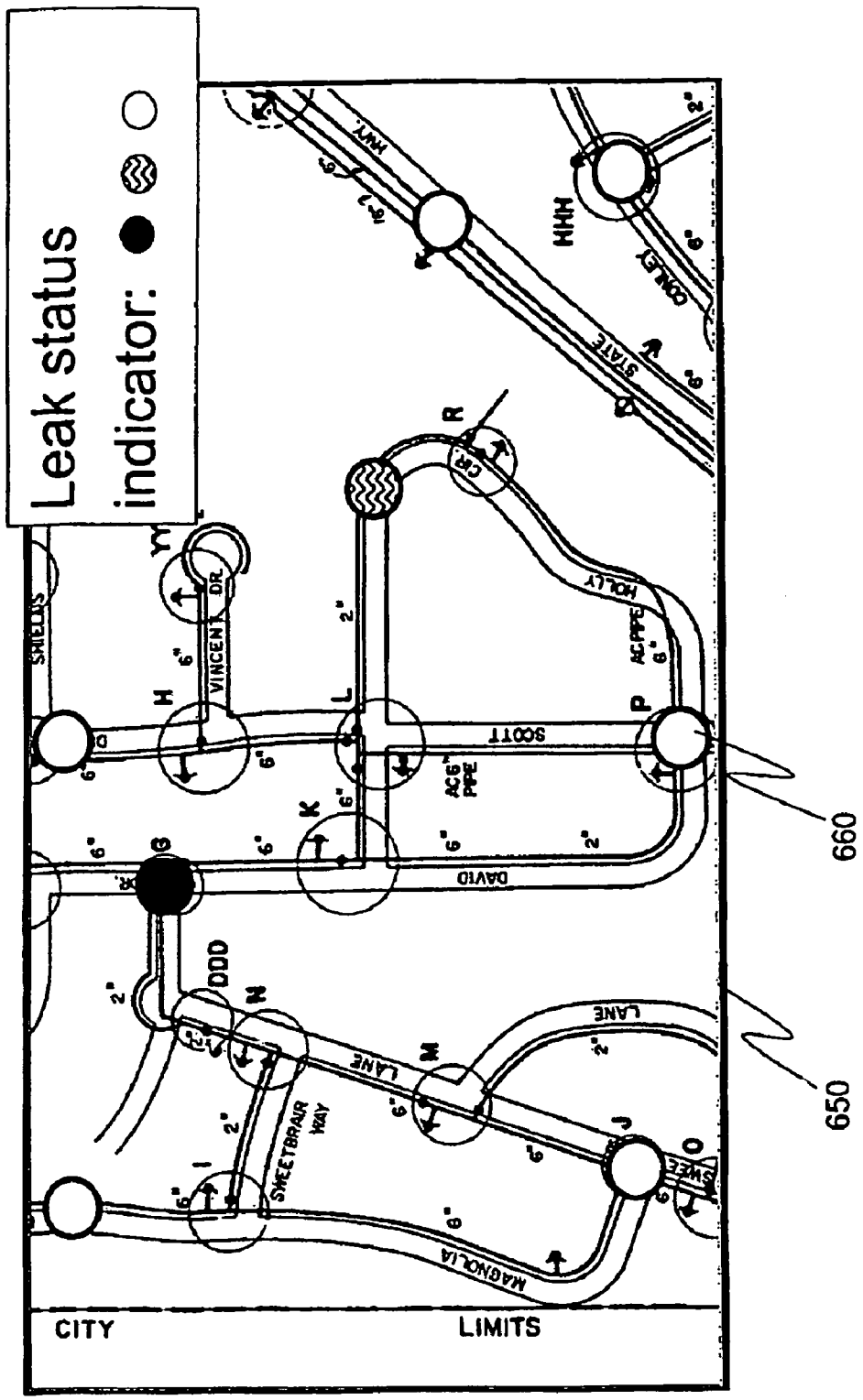
FIG. 11 is a map with symbols used to represent the positions of recorders on the map.

It is often advantageous to present information about the leak status of many recorders in the context of maps showing the areas in which the recorders are installed. Referring to FIG. 11, a map 650 includes symbols 660 that represent the positions of recorders on the map. The symbols may be colorcoded to display the leak status of the recorder corresponding to the symbol. The leak status may be programmed to reflect a quantization of the leak index or any other quantitative parameter obtained from the recorders.

Figure 12:
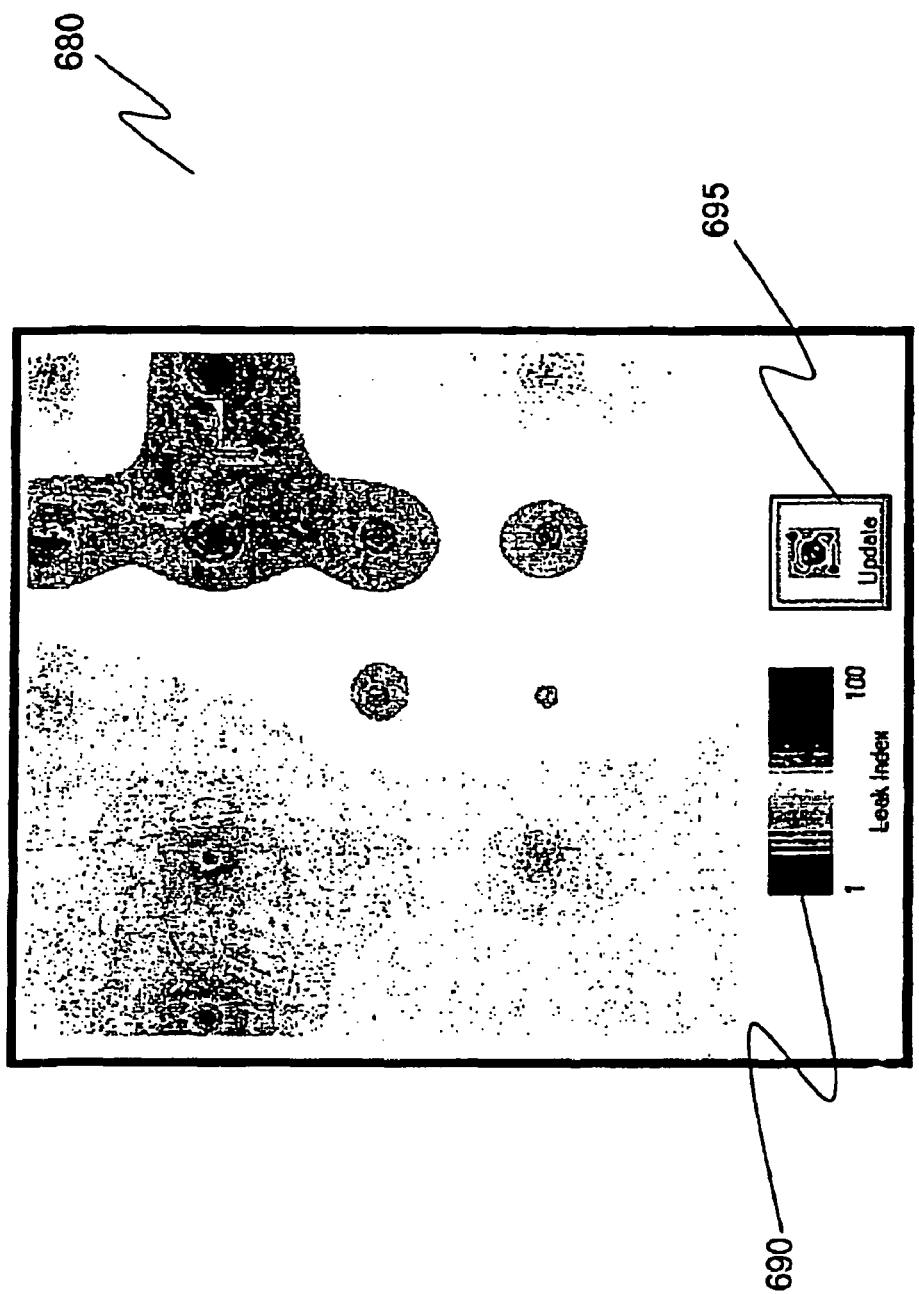
FIG. 12 is a solid color map showing a value of a leak index at all locations on the map.

Another useful method of visualizing information from many recorders in the context of maps showing the areas in which the recorders are installed is a solid color map. Referring to FIG. 12, a solid color map 680 shows a value of a leak index (or another quantitative parameter) at all locations on the map. The color at each location on the map is mapped to a particular value of the leak index using a color scale 690. With a solid color mapping of the leak index, the locations of all recorders present on the map may each be given the known leak index of the corresponding recorder. All other locations on the map may be given a computed value of the leak index that is extrapolated from the known values of the leak index of nearby recorders. This extrapolation may be performed using a number of well-known algorithms.

The solid color map 680 may be updated at any time under software control using, for example, an update button 695. The update feature is useful for varying the map scale, and the number of recorders and the geographical area included in the solid color map. The solid color map 680 allows visualizing the extent of vibrations recorded by one or more recorders. The solid color map 680 may be useful in computing and visualizing an approximate location of possible leaks using the vibration recordings of one or more recorders. The solid color map 680 may be overlaid and merged with details of aerial photographs, city maps, or maps of the pipeline system.

Figure 13:
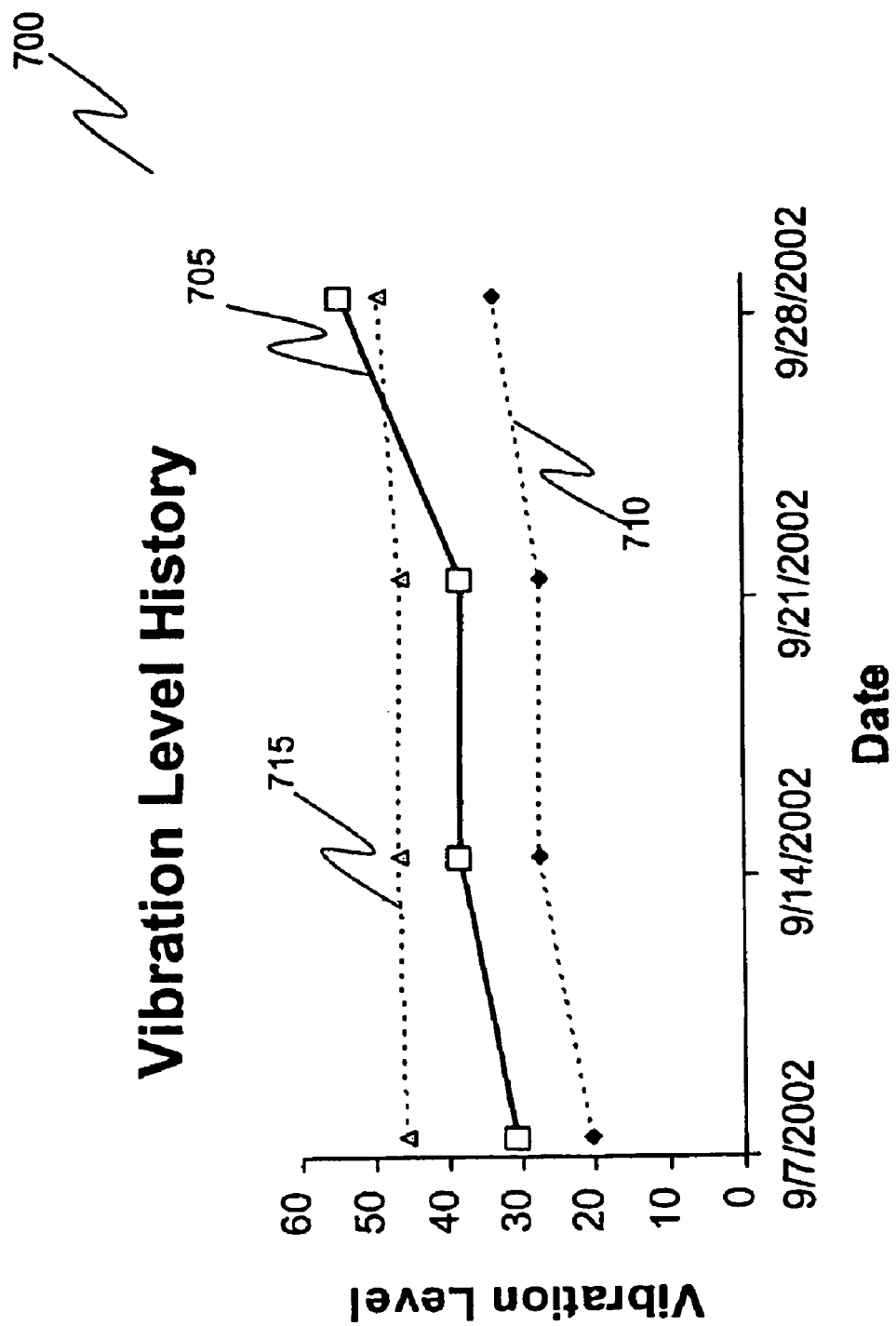
FIG. 13 is a graph showing the vibration level history of a single recorder of the system of FIG. 1.

Each recorder may also have a stored history of processed data. Referring to FIG. 13, a graph of vibration level history 700 may display a mean vibration level 705 together with a lower range measure 710 and an upper range measure 715. The lower and upper ranges may be computed from the history of processed data and represent estimates of the variation of the vibration level relative to the mean vibration level. The lower and upper range elements may also be omitted. Any historical quantitative parameter may be similarly displayed. The graph of vibration level history 700 is useful for visualizing changes that may have occurred over any available period of time in the vibration recordings of one or more recorders.

Figure 14:
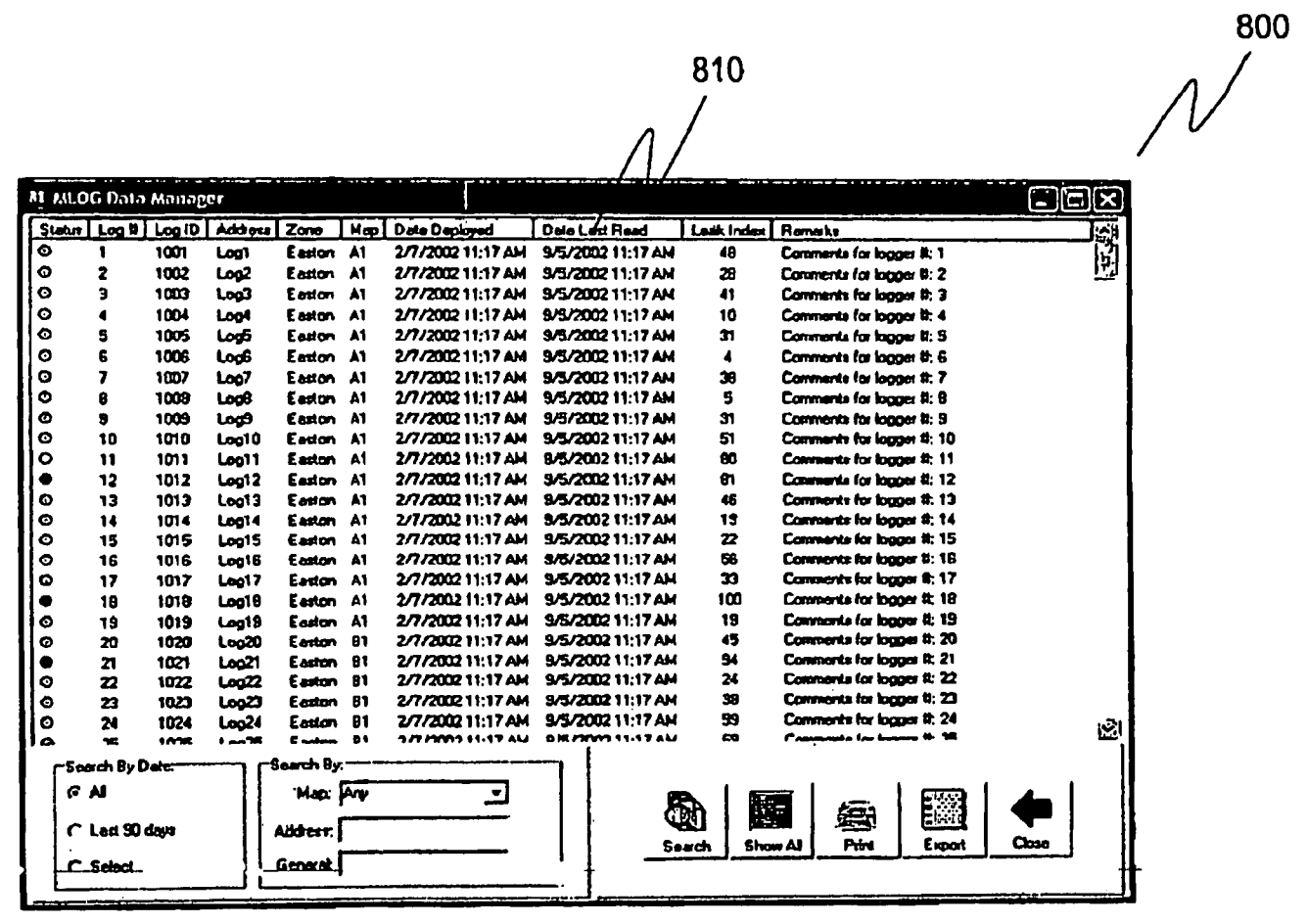

It may also be useful to select recorders according to some criteria based on the recorders' information profiles and processed vibration data. Referring to FIG. 14, a database table 800 may show parameters of the recorders, including, for example, leak index, leak status, map, address, and remarks entered by the system user. These parameters may be arranged in a database table that can be printed or exported to other software. Any subset of recorders can be defined, based on selecting particular values, or ranges of values of the parameters that are organized as the columns 810 of the database table 800. The columns may be sorted in some useful order. Other database capabilities may be incorporated to aid in managing the installation or information profiles of the recorders, the analysis of the recorders' processed vibration data, or the investigation of leaks or other activity that will occur as a result of the analysis.

Reports may be generated electronically or may be printed in order to aid these management, analysis, and investigation activities. The components of a report may contain a map, a database table with selected parameters from a set or subset of recorders, and other elements such as a title, date, or signature line that may aid the management, analysis, and investigation activities.

Figure 15:
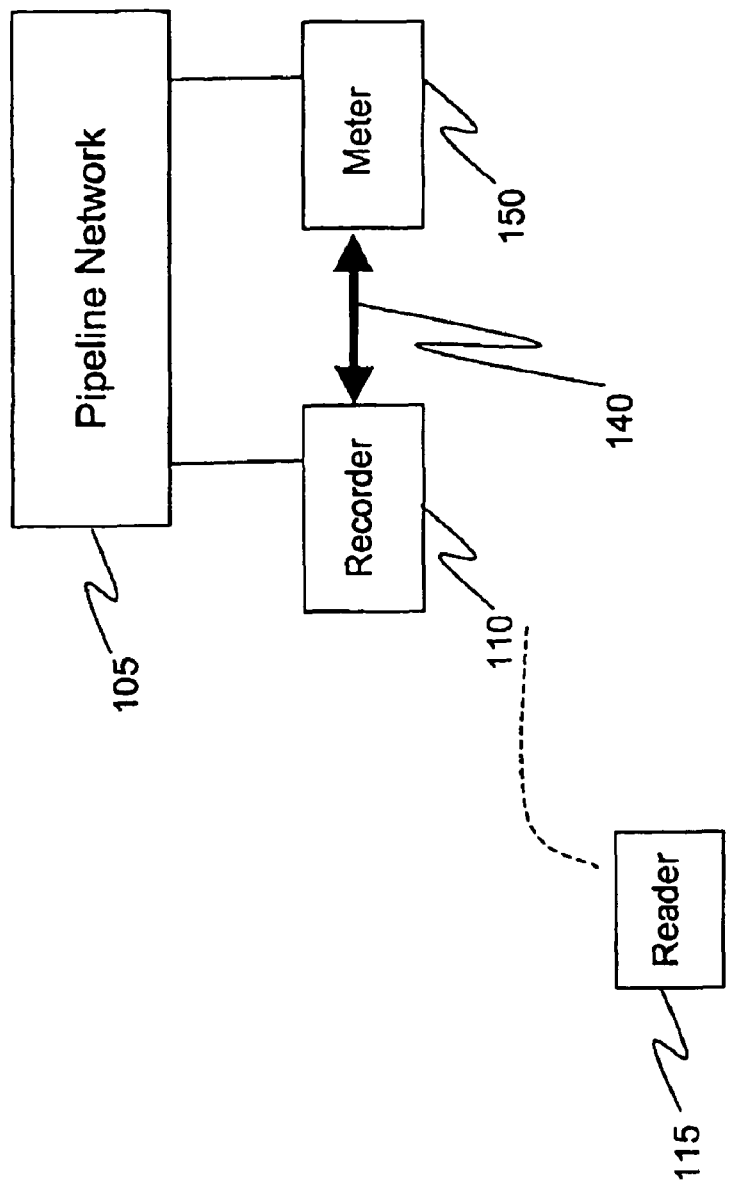
FIG. 15 is a block diagram of a system for tracking vibrations and meter readings in a pipeline network.

In another implementation, as illustrated in FIG. 15, a recorder 110 is connected permanently to a meter 150 through the meter's built-in electronic interface (MEI) 140. In a typical 3-wire interface, the processor 310 of the recorder 110 provides power and a sequence of clock pulses on one wire to activate the MEI. The MEI responds by sending the current meter reading to the recorder using an industry-standard sequence of characters on a second wire. For example, the MEI may reply to the clock pulses by sending the sequence "RB1234,0,4". The sequence is encoded as a digital sequence of ones and zeros where a low voltage represents a zero and a high voltage represents a one. The recorder decodes this industry standard sequence as the current meter reading (indicated by "RB") being 1,234 U.S. gallons (indicated by "0,4"). The third wire is an electrical common wire. Other implementations may provide a connection between the processor and the meter using electronic interfaces such as those using one or two wires, or using wireless interfaces. In yet other implementations, the recorder and the meter may be a single, integrated unit.

The recorder converts the output of the MEI 140 to a binary number and saves this number in the memory of the processor 310. The recorder may be programmed to read the meter using the MEI at specific times or specific time intervals.

By reading the meter value through the MEI at regular intervals (e.g., every 4 hours), the recorder can create a history of usage or consumption of the metered product, which might for example be water, gas, petroleum, or another pipeline fluid. The history of usage— or the usage profile—can be stored in the memory of the processor. The processor may be programmed to encode the values of the profile in order to conserve memory space and to store the profile more efficiently for subsequent transmission by the radio transceiver 320. One useful encoding scheme includes computing the difference between successive meter readings, denoted by x. If x ranges from 0 to 64,000, taking 16 bits of digital memory, then the value of x can be encoded by the transformation, $N=\log_2(x)$. The parameter N is a representation of x that requires only 4 bits of digital memory with the loss of some resolution of x. The sequence of values of N represents the usage profile, or pattern of usage of product passing through the meter. This sequence may be stored for a programmable time (e.g., 30 days). Subsequent values of N replace the oldest values to allow the most recent 30 days of data to be stored. The usage profile may be used to detect, for example, leaking appliances in a residential application.

By reading the meter value through the MEI at frequent intervals (e.g., every minute), the recorder can store data that is useful for assessing the pattern of activity at the meter. In one implementation, the difference in successive meter readings, x, can be used to create a meter pattern, y, as follows. If x is equal to zero there is either no flow through the meter or the flow was below the measurement resolution of the meter. This condition is denoted by y=0. If x is greater than zero, the meter has registered flow. This condition is denoted by y=1. In a 24-hour period there are 1,440 minutes. The meter pattern, y, is therefore represented by a series of 1,440 bits, with each bit having the value of zero or one, with the first value being measured at midnight. The meter pattern can be used to assess whether flow is approximately continuous or intermittent, at what time of the day or night flow is occurring, and whether any flow at all is occurring in the 24-hour period. The meter pattern, y, for any 24-hour period may be discarded as data from a new 24-hour period becomes available or it may be saved in the memory of the processor.

The meter pattern can also be used to assess the integrity of the meter or the security of the pipeline network. If the difference in successive meter readings, x, is negative, then the meter is registering flow in the reverse direction, i.e. flow into the pipeline network from the consumer's side of the meter. If this condition is encountered, then the starting time, duration, and quantity of reverse flow can be noted and saved in the memory of the processor. Unusual or unexpected patterns of meter activity can be detected by examination of the meter pattern under program control of the processor. For example, unexpected time periods of zero flow may indicate tampering or unauthorized bypassing of the meter. Unexpected periods of low or high flow may indicate a failure in the integrity or accuracy of the meter. Protracted or unexpected nighttime meter patterns may indicate a leak downstream of the meter or unintended usage by the consumer. The processor may be configured to generate and transmit an alert indication in response to any or all of these or similar conditions. The alert may be transmitted to any reader 115 that is within range. The reader 115 may be a handheld or vehicle-mounted device, or, in some cases, a unit permanently installed, for example, on a building roof or a utility pole.

The usage profile and the meter pattern stored by the processor may be transmitted to a reader 115 in the manner described previously. For example, the reader may transmit a PING to any recorder present in a specific form to request that the recorder transmit its processed results from vibration recordings, the computed usage profile, the computed meter pattern, an immediate meter reading, or any combination of these data.

Subsequent analysis of the usage profile transferred from the reader 115 to the computer 120 may be used to investigate the significance of the processed results of vibration recordings. For example, abnormal vibration energy and an unexpectedly high nighttime flow through the meter could indicate a leak that is downstream of the meter. Conversely, abnormal vibration energy and zero or normal nighttime flow could indicate a leak that is upstream of the meter. In another instance, normal vibration energy and continuous flow through the meter could indicate intended usage since the absence of abnormal vibration energy at the quietest time of the night indicates that flow was not present for an arbitrary period, which rules out a leak. Therefore, joint analysis of the processed results of vibration recordings and the usage profile provides additional benefits over these measurements considered separately. Analysis of vibration recordings and usage profiles from multiple recorders may be provide further insights and benefits.

Subsequent analysis of the meter patterns transferred to the computer 120 may be used to inform the consumer of unusual or problematic meter patterns. Analysis of the meter patterns may also be used to detect theft or unauthorized usage, such as excessive irrigation usage from a pipeline system conveying fresh water.

The architecture of the system 100 described provides additional benefits. The recorder may be connected to other types of devices than meters, such as pressure measuring devices, water quality monitors, valves, and other appurtenances and instrumentation connected to a pipeline system. In addition, the reader 115 may be programmed by the computer 120 to use its radio transponder 500 to transmit a new software program to the processor 310 without requiring a user to have physical access to the recorder. Such reprogramming of the processor will be useful if the meter type connected to the recorder is changed, if the recorder is to be connected to a different device, or if it is desirable to change or add an additional feature to the program of the processor. This capability may provide substantial savings to the user as new needs become apparent during the long life of the recorders.

Figure 16:
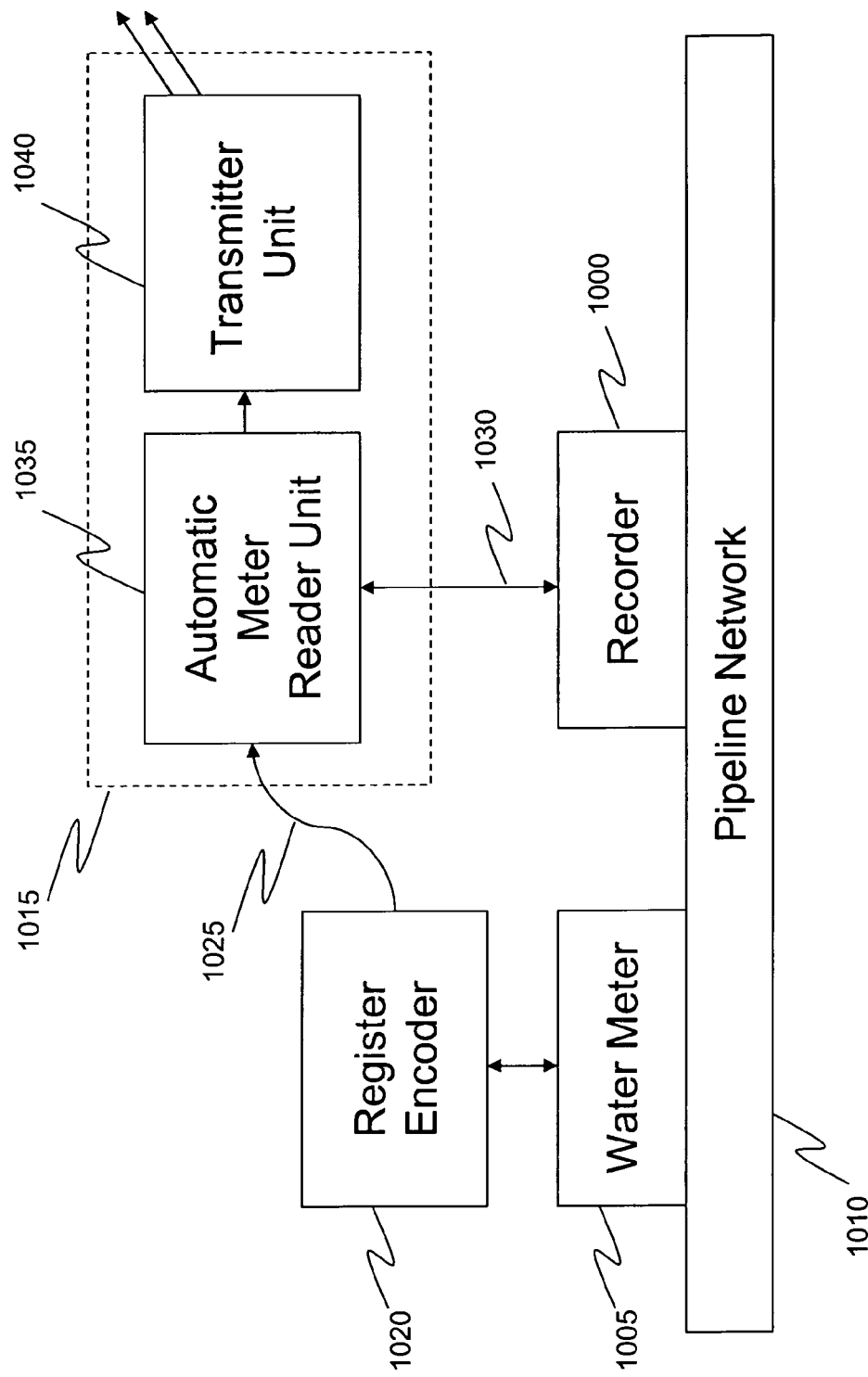
FIG. 16 is a block diagram of a system in which an automatic meter reader/transmitter collects data from both a water meter and a vibration recorder.

Referring to FIG. 16, in another implementation, a recorder 1000 and a water meter 1005 are connected to a pipeline network 1010. The recorder 1000 operates in manner similar to the recorder 110 to produce data about the pipeline network 1010. The recorder 1000 provides this data to an automatic meter reader/transmitter (AMRT) 1015.

The water meter 1005 measures flow in the pipeline network 1010. For example, the water meter 1005 may measure flow through one portion of the pipeline network 1010, such as a pipe feeding into a business or a residence.

In one type of water meter, a paddle wheel inside the water meter makes one complete revolution in response to the flow of a unit quantity of water through the water meter. For instance, certain domestic water meters are calibrated to, for example, 0.01 gallon per revolution. Water meters of different sizes or different types may be calibrated to some other volumetric measure, such as a fraction of a cubic foot. The paddle wheel generates a magnetic pulse for each revolution using an attached magnet.

Magnetic pulses generated by the water meter 1005 and representing unit quantities of flow through the water meter can be counted by a register encoder 1020 that also communicates with the AMRT 1015. The register encoder 1020 is typically mounted directly on top of the water meter in order to sense the magnetic pulses generated by the water meter. The register encoder contains electronics which maintain a count of the total number of magnetic pulses and hence a measure of the accumulated flow through the water meter. The value of the accumulated flow through the meter, that is the meter reading, is often displayed numerically on a set of mechanical wheels. This value is a measure of the positive accumulated flow, which may be, for example, flow from the water distribution system that includes the pipeline network 1010 through the meter 1005 for consumption.

The register encoder may also be capable of registering accumulated reverse flow through the meter 1005 (i.e., flow from the consumer's side of the water meter into the water distribution system that includes the pipeline network 1010). Such a measure may be useful to monitor the integrity of the treated water flowing in the water distribution system.

In the illustrated implementation, the AMRT 1015 is connected to the register encoder 1020 and the recorder 1000 by industry-standard, 3-wire cable interfaces 1025 and 1030. The interfaces 1025 and 1030 may be implemented using the interface described in the Register Interface Specification, document UI-1203, release 1.8, dated Feb. 18, 2002 (Sensus Metering Systems, Inc., Raleigh, N.C.). Other implementations may employ different connections, including wired and wireless connections.

The AMRT 1015 includes an automatic meter reader unit 1035 that is connected to a transmitter unit 1040. The AMRT is typically mounted to the basement rafters at indoor mounting sites, in order to facilitate wireless communication with remote points. At outdoor mounting sites, the AMRT is typically mounted to the underside of a non-metallic cover covering an underground meter pit.

The AMRT 1015 may read a value stored in the register encoder 1020 at a pre-programmed time using the automatic meter reader unit 1035 and the interface 1025. The AMRT 1015 may collect data from the recorder 1000 at the same or other times using the automatic meter reader unit 1035 and the interface 1030. For example, the automatic meter reader unit 1035 may read the recorder 1000 at regular intervals. The process of reading the recorder by the AMRT can be substantially similar to the process of reading a register encoder by the AMRT. To this end, the recorder may be further programmed to emulate a particular type of register encoder. Specifically, for example, the recorder may output a sequence of characters such as ";RB123456<CR>". This character sequence is defined in the Register Interface Specification reference identified above and is interpreted as follows:

;—designates the start of a new message;

RB—indicates that the value is an accumulated flow value (meter reading);

123456—a value which may be interpreted as a 6-digit flow meter reading, for example, 123,456 gallons; and <CR>—designates the end of the message.

Based on knowledge that this sequence of characters was provided by a recorder rather than a register encoder, the sequence of characters can later be interpreted in a manner consistent with recorder data (e.g., 123456 can be interpreted as a data value indicating a particular sensor parameter).

From the point of view of the AMRT, the process of reading the recorder is identical and indistinguishable from the process of reading the register encoder. A value read from a recorder associated with an AMRT device may be transmitted in the normal way by the transmitter unit of the AMRT. As a result, recorders may be incorporated into an automatic meter reading system without altering the software or hardware used to collect the meter reading values. As discussed in more detail below, the values are transmitted to a signal receiving unit and then sent to a computer. A software program running on the computer allows for processing of values that are identified as originating from recorders, as opposed to register encoders. Values collected from multiple recorders may be analyzed to detect vibrations and related phenomena (e.g., leaks) in the pipeline network.

The recorder may be further programmed to vary the value which will be read by the automatic meter reader unit at any particular time. In this manner the recorder may take advantage of frequent reading operations by the AMRT to send several values to the computer in a 24-hour period. The sent values may be combined to create more information for analysis from each recorder.

The meter value and sensor data read by the automatic meter reader unit 1035 may subsequently be transmitted using the transmitter unit 1040. For example, certain implementations may perform the transmission in response to a radio signal received from a passing vehicle in a procedure that may be referred to as "drive-by" meter reading, while other implementations perform the transmission using a "fixed-installation" meter reading process in which transmissions occur at approximately regular time intervals, such as, for example, one transmission every six hours.

Figure 17:
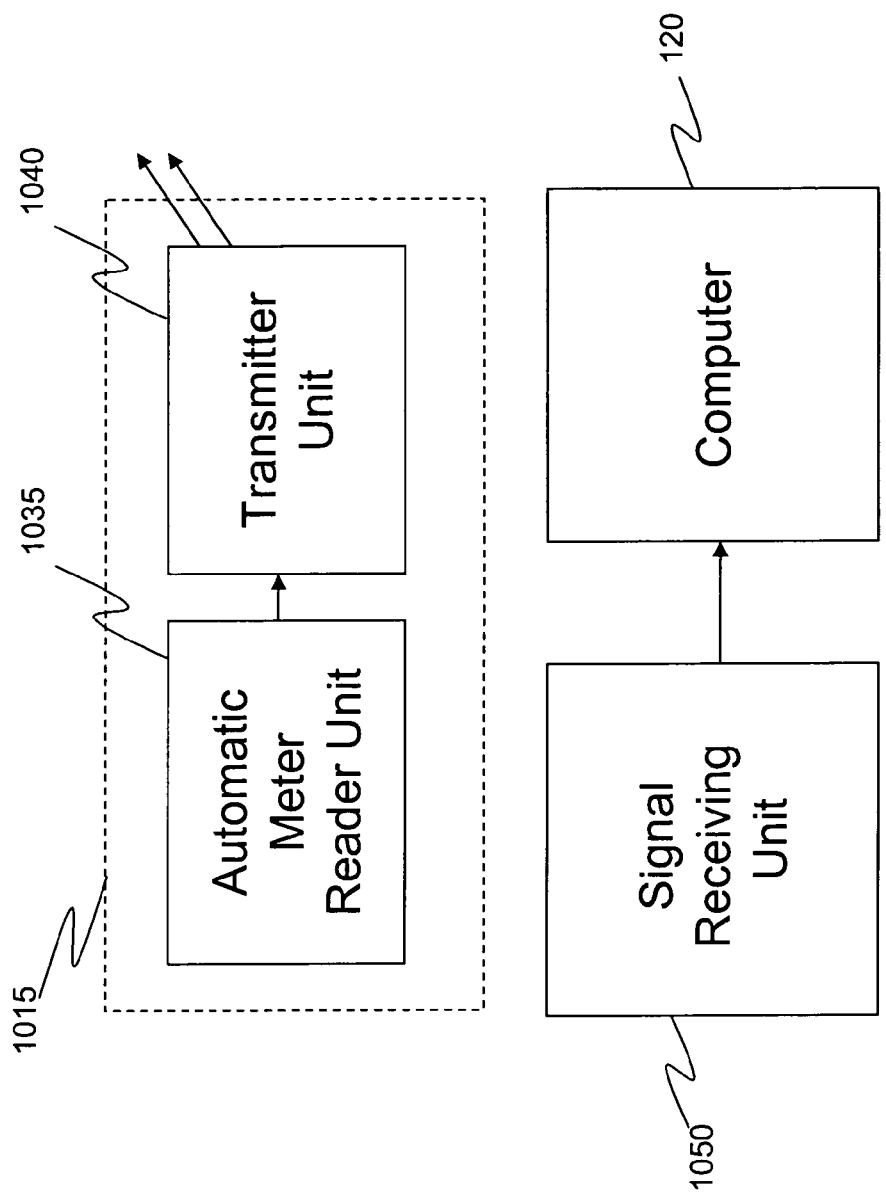
FIG. 17 is a block diagram of a system in which an automatic meter reader/transmitter communicates with a signal receiving unit and a computer.

Referring to FIG. 17, a signal receiving unit 1050 collects meter reading values and other data from multiple AMRT devices 1020 associated with individual water meters. The receiving unit 1050 may be, for example, a unit mounted in a vehicle (in a "drive-by" meter reading process) or a unit that is one of many units installed at points throughout the pipeline network 1010 (in a "fixed-installation" meter reading process). Values and data collected from multiple AMRT devices 1020 are subsequently sent to a computer, such as the computer 120 discussed above.

The computer 120 runs software that processes values from multiple register encoders that are connected to individual water meters. One purpose of this processing is to facilitate billing customers for water usage through individual water meters. Another purpose is to provide information about the patterns of consumption of water through individual meters and through the water distribution system.

Figure 18:
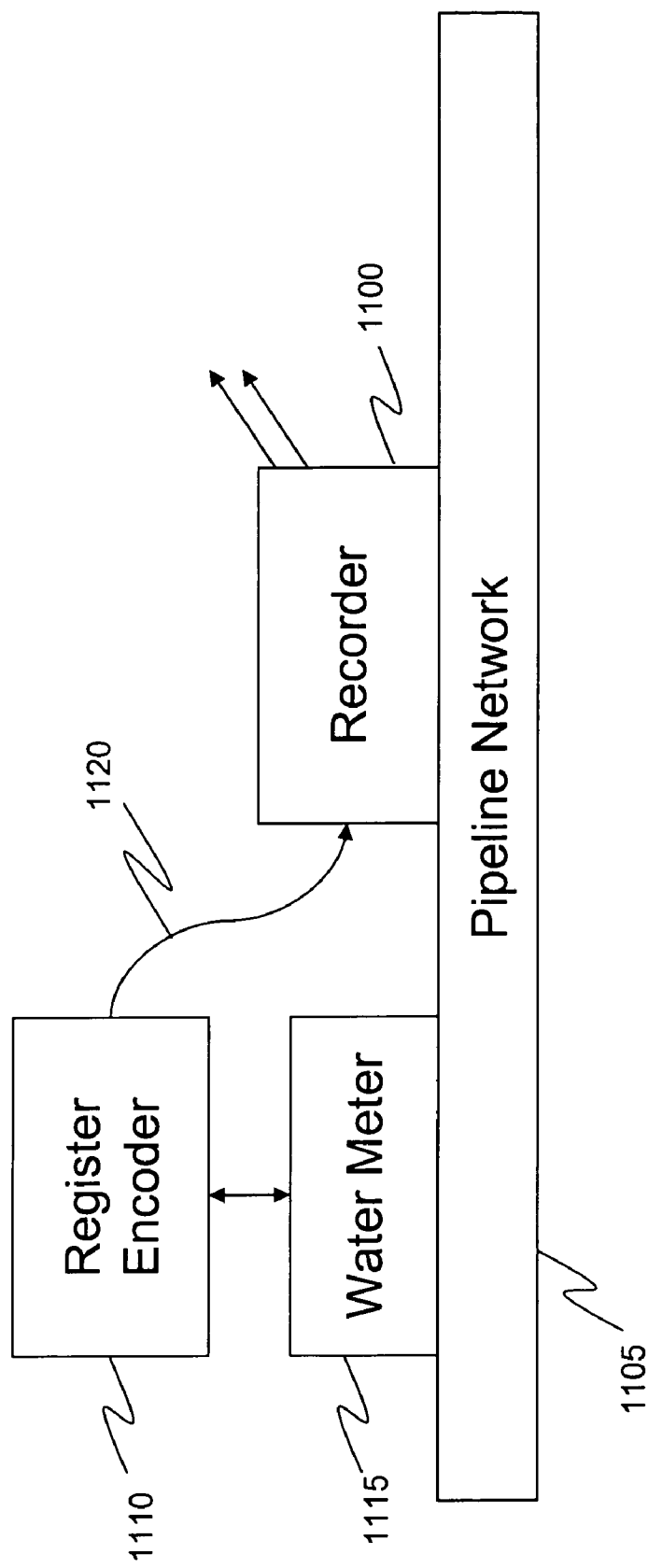
FIG. 18 is a block diagram of a system in which a vibration recorder collects readings from a water meter.

Referring to FIG. 18, a recorder 1100 is connected to a pipeline network 1105. The recorder 1100, which has properties similar to those discussed above with respect to recorders 110 and 1000, collects meter reading values from a register encoder 1110 of a water meter 1115 through a cable interface 1120. The processor of the recorder may be programmed to read a value from the register encoder at regular intervals. Values read from the register encoder can be stored in the memory of the recorder. The processor of the recorder may be further programmed to recognize automatically the type of register encoder and the format of the value output by the register encoder. This allows replacement of a register encoder at a water meter without the need to reprogram the associated recorder.

The recorder 1100 may include a radio transceiver that is used to transmit meter readings and processed vibrations. A reader, such as the reader 115 discussed above, when brought into proximity with the recorder 1100, collects data from the recorder 1100. The readers later downloads the meter readings and processed vibrations to a computer, such as a computer 120, in the manner discussed above.

In other implementations, instead of communicating with the reader, the recorder 1100 communicates with an AMRT in the manner discussed above. Alternatively, the functionality of the AMRT device may be incorporated into the recorder, and the recorder may communicate with the receiver unit. This capability may be useful for facilitating analysis of water usage when the AMRT device is read using a "drive-by" meter reading procedure.

The computer jointly processes the meter readings and processed vibrations from multiple recorders and meters to detect leaks and to determine the side of the water meter on which a leak is located. For example, abnormal vibrations during periods of low or normal flow through the meter are indicative of a leak location on the upstream side of the meter, while abnormal vibrations during periods of abnormally high and constant flow through the meter are indicative of a leak location on the downstream side of the meter.

Figure 19:
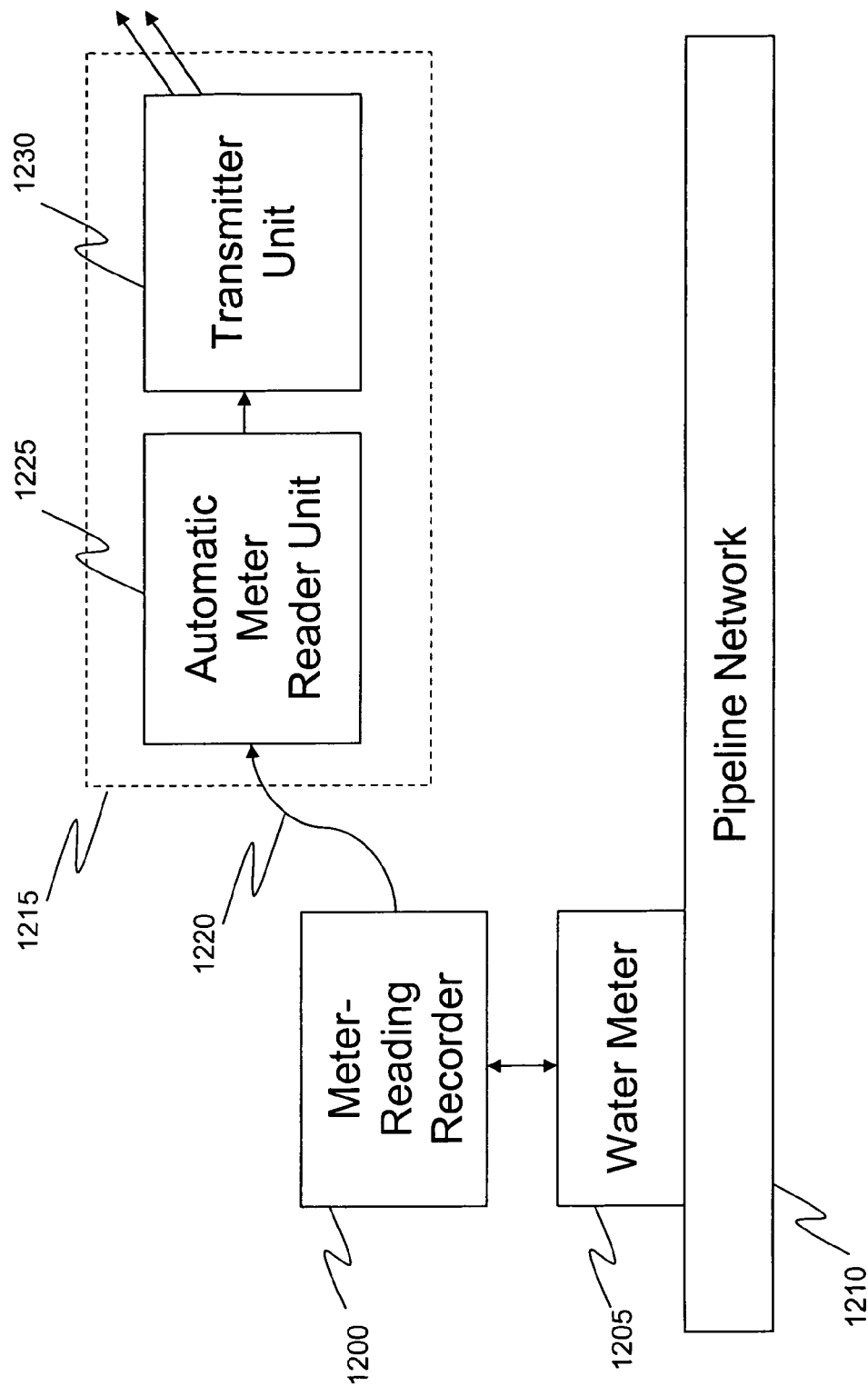
FIG. 19 is a block diagram of a system in which a meter-reading recorder communicates with an automatic meter reader/transmitter.

Referring to FIG. 19, the capability of detecting magnetic pulses may be readily incorporated into a vibration recorder to create a meter-reading recorder 1200 that detects pulses produced by a water meter 1205 connected to a pipeline network 1210. The processor of the meter-reading recorder may be programmed to detect and count pulses indicative of both positive and negative flow. The processor may also be programmed to register periods of zero flow through the water meter 1205. Such a measure may be useful to detect tampering with the water meter by analyzing patterns of water usage. The meter-reading recorder includes the capabilities of both a vibration recorder, such as the vibration recorder 110 discussed above, and a register encoder, such as the register encoder 1020 discussed above.

The meter-reading recorder 1200 may be connected to an AMRT device 1215 through a cable interface 1220. The AMRT device 1215 may read a value presented by the recorder at a pre-programmed time using an automatic meter reader unit 1225. The recorder may variously present either meter reading values or processed vibration values to the AMRT. The values read by the automatic meter reader unit may subsequently be transmitted using a transmitter unit 1230, received by a signal receiving unit, such as the signal receiving unit 1050, and sent to a computer, such as the computer 120, for subsequent analysis.

Figure 20:
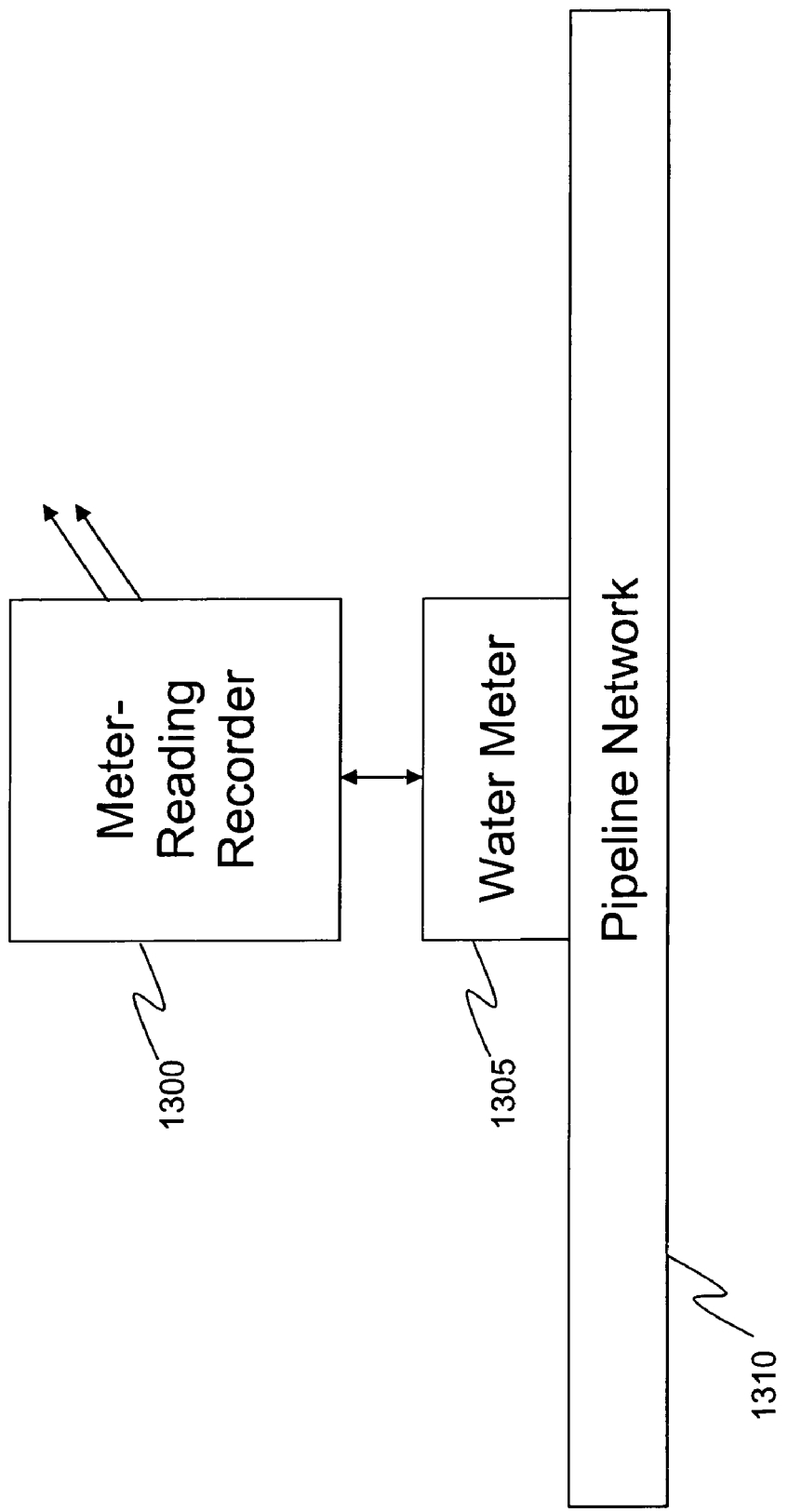
FIG. 20 is a block diagram of a system in which a meter-reading recorder provides the functions of an automatic meter reader/transmitter.

Referring to FIG. 20, a meter-reading recorder 1300 may be configured to perform the functions of a recorder, such as the recorder 110 discussed above; a register encoder, such as the register encoder 1020 discussed above; and an AMRT, such as the AMRT 1015 discussed above. To this end, the recorder 1300 may be programmed to detect and count pulses from a water meter 1305 connected to a pipeline network 1310, and to transmit both meter readings and processed vibrations.

A number of implementations have been described. Nevertheless, it will be understood that various modifications may be made. Accordingly, other implementations are within the scope of the following claims.

What is claimed is:

1. A vibration recorder for detecting leaks in a pipeline network, the vibration recorder comprising:
   a sensor operable to receive vibration signals from a pipeline network;
   a communication port connected to an automatic meter reader/transmitter ("AMRT") that is configured to receive meter reading values; and
   a processor connected to the communication port and to the sensor to receive the vibration signals, the processor being programmed to process the vibration signals and to send data regarding the processed vibration signals to the AMRT using the communication port; and
   wherein the AMRT is configured to transmit the data regarding the processed vibration signals and the meter reading values.

2. The vibration recorder of claim 1 wherein the processor is programmed to emulate a register encoder of a water meter when sending data to the AMRT.

3. The vibration recorder of claim 1 wherein the processor is programmed to send data regarding the processed vibration signals to the AMRT as a sequence of meter reading values.

4. The vibration recorder of claim 1, further comprising a connection to a register encoder of a water meter, wherein the processor is programmed to receive the meter reading values from the connection to the register encoder and to send the meter reading values to the AMRT.

5. The vibration recorder of claim 4 wherein the processor is programmed to determine a type of the register encoder.

6. The vibration recorder of claim 5 wherein the processor is programmed to interpret the meter reading values received from the connection to the register encoder based on the determined type of the register encoder.

7. The vibration recorder of claim 4 wherein the processor is programmed to determine a usage activity pattern based on the meter reading values.

8. The vibration recorder of claim 1, further comprising a pulse detector configured to detect magnetic pulses produced by a water meter, wherein the processor is connected to receive an output of the pulse detector and programmed to generate the meter reading values based on the output of the pulse detector.

9. The vibration recorder of claim 8 wherein the processor is programmed to determine a usage activity pattern based on the output of the pulse detector.

10. A vibration recorder for detecting leaks in a pipeline network, the vibration recorder comprising:
    a sensor operable to receive vibration signals from a pipeline network;
    a wireless transmitter;
    a processor connected to the wireless transmitter and to the sensor to receive the vibration signals, the processor being programmed to process the vibration signals and to use the transmitter to transmit data regarding the processed vibration signals, and to generate meter reading values and to use the transmitter to transmit the meter reading values; and
    a connection to a register encoder of a water meter, wherein the processor is programmed to generate the meter reading values based on data received from the register encoder.

11. The vibration recorder of claim 10 wherein the processor is programmed to determine a type of the register encoder.

12. The vibration recorder of claim 11 wherein the processor is programmed to interpret the data received from the connection to the register encoder based on the determined type of the register encoder.

13. The vibration recorder of claim 10 wherein the processor is programmed to determine a usage activity pattern based on the data received from the connection to the register encoder.

14. A vibration recorder for detecting leaks in a pipeline network, the vibration recorder comprising:
    a sensor operable to receive vibration signals from a pipeline network;
    a wireless transmitter;
    a processor connected to the wireless transmitter and to the sensor to receive the vibration signals, the processor being programmed to process the vibration signals and to use the transmitter to transmit data regarding the processed vibration signals, and to generate meter reading values and to use the transmitter to transmit the meter reading values; and
    a pulse detector configured to detect magnetic pulses produced by a water meter, wherein the processor is connected to receive an output of the pulse detector and programmed to generate meter reading values based on the output of the pulse detector.

15. The vibration recorder of claim 14 wherein the processor is programmed to determine a usage activity pattern based on the output of the pulse detector.

* * * * *